(12) United States Patent
Westesen et al.

(10) Patent No.: US 6,207,178 B1
(45) Date of Patent: *Mar. 27, 2001

(54) SOLID LIPID PARTICLES, PARTICLES OF BIOACTIVE AGENTS AND METHODS FOR THE MANUFACTURE AND USE THEREOF

(75) Inventors: Kirsten Westesen, Konigslutter/Bornum; Britta Siekmann, Braunschweig, both of (DE)

(73) Assignee: Kabi Pharmacia AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/204,075

(22) Filed: Dec. 3, 1998

Related U.S. Application Data

(63) Continuation of application No. 08/757,276, filed on Dec. 2, 1996, now Pat. No. 5,885,486, which is a continuation of application No. 08/226,471, filed on Apr. 12, 1994, now Pat. No. 5,785,976, which is a continuation-in-part of application No. 08/141,058, filed on Oct. 26, 1993, now abandoned, which is a continuation-in-part of application No. 08/027,501, filed on Mar. 5, 1993, now abandoned.

(51) Int. Cl.$^7$ .............................. A01N 25/04; A61K 9/10; A61K 9/19; B01F 3/12
(52) U.S. Cl. .................. 424/405; 252/363.5; 264/4.4; 424/400; 424/497; 424/498; 504/362; 514/937; 514/964; 516/77; 516/926; 516/928
(58) Field of Search .................. 264/4.4; 252/363.5; 427/213.31, 213.36; 428/402.24; 424/497, 498, 400, 405; 514/937, 362, 964; 516/77, 926, 928

(56) References Cited

U.S. PATENT DOCUMENTS

| | | | |
|---|---|---|---|
| 3,993,754 | 11/1976 | Rahmann et al. | 424/450 X |
| 4,235,871 | 11/1980 | Papahadjopoulos et al. | 424/450 |
| 4,280,996 | 7/1981 | Okamoto et la. . | |
| 4,356,167 | 10/1982 | Kelly | 424/450 |
| 4,610,868 | 9/1986 | Fountain et al. | 264/4.1 X |
| 4,931,284 | * 6/1990 | Ekman et al. | 424/450 |
| 4,973,465 | * 11/1990 | Baurain et al. | 424/498 X |
| 5,091,187 | * 2/1992 | Haynes | 424/450 |
| 5,785,976 | * 7/1998 | Westesen et al. | 424/400 |
| 5,885,486 | * 3/1999 | Westesen et al. | 516/77 X |

FOREIGN PATENT DOCUMENTS

| | | |
|---|---|---|
| 0 167 825 | 8/1990 | (EP) . |
| WO 91/02517 | 3/1991 | (WO) . |

OTHER PUBLICATIONS

Eldem et al., Pharm. Res. 8, pp. 47–54, 1991.
T. Eldem et al., Pharm. Res. 8, pp. 178–184, 1991.
K. Larsson, Acta Chem. Scand. 20, pp. 2255–2260, (1966).
B. Seikmann and K. Westesen, Pharm. Pharmacol. Lett. 1, pp. 123–126, 1992.

* cited by examiner

Primary Examiner—Richard D. Lovering
(74) Attorney, Agent, or Firm—Pepper Hamilton LLP; Gilberto M. Villacorta; Corinne M. Pouliquen

(57) ABSTRACT

The present invention is in the area of administration forms and delivery systems for drugs, vaccines and other biologically active agents. More specifically the invention is related to the preparation of suspensions of colloidal solid lipid particles (SLPs) of predominantly anisometrical shape with the lipid matrix being in a stable polymorphic modification and of suspensions of micron and submicron particles of bioactive agents (PBAs); as well as to the use of such suspensions or the lyophilizates thereof as delivery systems primarily for the parenteral administration of preferably poorly water-soluble bioactive substances, particularly drugs, and to their use in cosmetic, food and agricultural products.

SLPs and PBAs are prepared by the following emulsification process:

(1) A solid lipid or bioactive agent or a mixture of solid lipids or bioactive agents is melted.
(2) Stabilizers are added either to the lipid or bioactive agent and to the aqueous phase or to the aqueous phase only depending on their physicochemical characteristics. Stabilizers may also be added or exchanged after homogenization.
(3) Drugs or other bioactive substances to be incorporated into the SLPs may be melted together with the lipids if the physicochemical characteristics of the substance permit or may be dissolved, solubilized or dispersed in the lipid melt before homogenization.
(4) The aqueous phase is heated to the temperature of the melt before mixing and may contain for example stabilizers, isotonicity agents, buffering substances, cryoprotectants and/or preservatives.
(5) The molten lipid compounds and the bioactive agents are emulsified in an aqueous phase preferably by high-pressure homogenization.

5 Claims, 13 Drawing Sheets

SOLID LIPID PARTICLES, PARTICLES OF BIOACTIVE AGENTS AND METHODS FOR THE MANUFACTURE AND USE THEREOF

RELATED APPLICATIONS

The present application is a continuation of U.S. application Ser. No. 08/757,276, filed Dec. 2, 1996 and now U.S. Pat. No. 5,885,486, which in turn is a continuation of U.S. application Ser. No. 08/226,471, filed Apr. 12, 1994, and now U.S. Pat. No. 5,785,976, which in turn is a continuation in part of U.S. application Ser. No. 08/141,058, filed Oct. 26, 1993, and now abandoned, which in turn is a continuation in part of Ser. No. 08/027,501, filed Mar. 5, 1993, and now abandoned, the entire disclosures of which are incorporated by references herein.

This invention relates to suspensions of particles of biodegradable lipids solid at room temperature, preferably triglycerides, which can be used as carriers for poorly water soluble drugs or other bioactive agents, and to suspensions of particles constituted by biologically active agents such as drugs, insecticides, fungicides, pesticides, herbicides and fertilizers, as well as to the lyophilizates thereof. Both systems can be prepared by a melt emulsification process.

The properties of the solid lipid particles (SLPs) include biodegradability, avoidance of toxicologically active residues from the production process, enhanced physicochemical stability with regard to coalescence and drug leakage, modified surface characteristics, controlled release of incorporated substances and modified biodistribution. The particles can be prepared by an emulsification process of molten material creating liquid droplets which form crystalline anisometrical particles on cooling. The anisometrical particles are of micron and submicron size, predominantly in the size range from 50 to 500 nm. The described suspensions have several advantages over other drug carrier systems deriving from the solid biodegradable matrix being predominantly present in a β-polymorphic modification (e.g. β', $β_1$, $β_2$), and not in an amorphous or α-crystalline state.

The preparation of micron and submicron particles consisting of poorly water-soluble bioactive agents (PBAS) by emulsification of the molten substance presents a novel process to reduce the particle size and/or to modify the surface characteristics of powdered substances which can be accomplished by inexpensive techniques and by the use of physiologically acceptable additives only. The suspensions of the particles are an easy-to-handle product from the security point of view. The particles of bioactive agents provide for the modified biodistribution and bioavailability of the formulated drugs or other bioactive substances which implies a modification of the extent and rate of dissolution and absorption, the circulation time, the site of action and the way of disposition of the drug or other bioactive substance. A reduction in particle size below the micrometer range provides for the direct intravenous administration of particles made from poorly water-soluble drugs without the need of a carrier vehicle.

FIELD OF THE INVENTION

The present invention is in the area of administration forms and delivery systems for drugs, vaccines and other biologically active agents such as insecticides, fungicides, pesticides, herbicides and fertilizers. More specifically, the invention is related to the preparation of suspensions of colloidal solid lipid particles (SLPs) with the lipid matrix being in a stable polymorphic modification and of suspensions of micron and submicron particles of bioactive agents (PBAs), as well as to the use of such suspensions or the lyophilizates thereof as delivery systems, primarily for the parenteral but also for the peroral, nasal, pulmonary, rectal, dermal and buccal administration of preferably poorly water-soluble bioactive substances, particularly drugs; and to their use in cosmetic, food and agricultural products. These suspension systems provide for the controlled release of incorporated or constituting substances as well as for the modified biodistribution and bioavailability of incorporated or constituting drugs, which implies a modification of the extent and rate of dissolution and absorption, the circulation time, the site of action and the way of disposition of the drug.

BACKGROUND OF THE INVENTION

The parenteral, in particular the intravenous administration of water-insoluble or poorly water-soluble substances such as drugs or other biological materials often presents a problem to the formulator. Since the diameter of the smallest blood capillaries is only a few microns the intravenous application of larger particles would lead to capillary blockage. Solid drug substances are, however, commonly disintegrated by milling and grinding, thereby generating particles from a few millimeters down to the micrometer size range which are too large to be injected directly as an aqueous suspension. As a consequence, intravenous administration systems containing suspended particles of water-insoluble drugs are not commercially available due to the risk of embolism. A further decrease in particle size is expensive, ineffective or even impossible by conventional techniques. Additionally, the reduction of solids to submicron-sized powders brings about heavy difficulties in handling these dry products such as an increased risk of dust explosions and cross-contamination problems in a factory environment. Moreover, such systems present a health risk for persons exposed to the possible inhalation and absorption of potent bioactive materials. Up to now the only possibilities to administer poorly water-soluble substances by the intravenous route are the use of co-solvents or the development of carrier systems which incorporate such substances in vehicles with hydrophilic surfaces.

Basic requirements of an ideal drug carrier system imply biodegradability, non-toxicity and non-immunogenicity. Moreover, the carrier should be suitable for the intended route of administration, e.g. with regard to particle size. Often a controlled release of the incorporated bioactive material is desired, for example when constant serum levels should be maintained over a long period of time or when the drug exhibits only a low therapeutic index.

Furthermore, carrier systems can be employed to prolong the half-life of certain substances which are unstable due to rapid enzymatic or hydrolytic degradation in biological milieu. On the other hand the incorporation of drug in the carrier material also presents an opportunity to protect the host from the drug in case of non-selective toxic substances such as antitumour agents.

In many cases drug carrier systems are developed with the object to deliver drugs to site-specific targets under circumvention of uptake by the reticuloendothelial system (RES). The rationale for such a drug targeting is an enhancement of the drug's therapeutic efficacy by an increase of the drug concentration at the target site with a simultaneous decrease at non-target sites, thereby rendering possible a reduction of the administered dose. Thus, the toxicity of drugs, e.g. anticancer agents, can be diminished, leading to a decrease of side effects.

The prerequisite of a successful site-specific delivery implies a certain selectivity of the carrier system for the target tissue as well as the accessibility of the desired target site. Targeting by the intravenous route of application is generally connected to an avoidance or at least a reduction of carrier uptake by the RES except for the cases where a direct targeting to cells of the RES is desired. Clearance of colloidal particles by the RES has been described to depend on particle size as well as on particle surface characteristics such as surface charge and surface hydrophobicity. In general, small particles are cleared less rapidly from the blood stream than large particles whereas charged particles are taken up more rapidly than hydrophilic non-charged particles. Due to these facts approaches to drug targeting are the modification of surface characteristics and the reduction of particle size.

Moreover, a small particle size is also required for the targeting of drugs to extravascular sites since extravasation is only feasible through a receptor-mediated uptake by phagocytosis/pinocytosis or where the endothelial wall is fenestrated. These fenestrations can be found for example in the sinusoids of liver, spleen and bone-marrow and show diameters of up to approximately 150 nm.

From the manufacturing point of view the ideal drug carrier system should be preparable without complications by easy-to-handle techniques in a reproducible manner and possibly at low production costs. The formulation should exhibit sufficient stability during preparation as well as on storage.

In recent years several colloidal systems have received special interest for their potential application as drug carriers, among them being liposomes, lipid emulsions, microspheres and nanoparticles. However, all of the systems mentioned possess a certain number of draw-backs which so far have prevented the break-through of any such system as a widespread, commercially exploited drug carrier.

Drug carrier systems in the micrometer size range are represented by microspheres consisting of a solid polymer matrix, and microcapsules in which a liquid or a solid phase is surrounded and encapsulated by a polymer film. Nanoparticles consist, like microspheres, of a solid polymer matrix. Their mean particle size, however, lies in the nanometer range. Both micro- and nanoparticles are generally prepared either by emulsion polymerization or by solvent evaporation techniques. Due to these production methods micro- and nanoparticles bear the risk of residual contaminations from the production process like organic solvents such as chlorinated hydrocarbons, as well as toxic monomers, surfactants and cross-linking agents, which may lead to toxicological problems. Moreover, some polymeric materials such as polylactic acid and polylactic-glycolic acid degrade very slowly in vivo so that multiple administration could lead to polymer accumulation associated with adverse side effects. Other polymers such as polyalkylcyanoacrylates release toxic formaldehyde on degradation in the body.

Drug carrier systems for parenteral administration based on lipids are liposomes and submicron lipid emulsions. Although such systems consist of physiological components only, thus reducing toxicological problems there is a number of disadvantages associated with these lipid carriers.

Liposomes are spherical colloidal structures in which an internal aqueous phase is surrounded by one or more phospholipid bilayers. The potential use of liposomes as drug delivery systems has been disclosed inter alia in the U.S. Pat. Nos. 3,993,754 (issued Nov. 23, 1976 to Rahmann and Cerny), 4,235,871 (issued Nov. 25, 1980 to Papahadjopoulos and Szoka) and 4,356,167 (issued Oct. 26, 1982 to L. Kelly). The major drawbacks of conventional liposomes are their instability on storage, the low reproducibility of manufacture, the low entrapment efficiency and the leakage of drugs.

According to the IUPAC definition, in an emulsion liquids or liquid crystals are dispersed in a liquid. Lipid emulsions for parenteral administration consist inter alia of liquid oil droplets, predominantly in the submicron size range, dispersed in an aqueous phase and stabilized by an interfacial film of emulsifiers. Typical formulations are disclosed in the Jap. Pat. No 55,476/79 issued May 7, 1979 to Okamota, Tsuda and Yokoyama. The preparation of a drug containing lipid emulsion is described in WO 91/02517 issued Mar. 7, 1991 to Davis and Washington. The susceptibility of these lipid emulsions towards the incorporation of drugs is relatively high due to the mobility of drug molecules within the internal oil phase since diffusing molecules can easily protrude into the emulsifier film causing instabilities which lead to coalescence. Furthermore, release of incorporated drugs from lipid emulsions is relatively fast so that the possibilities for a sustained drug release are limited.

Fountain et al (U.S. Pat. No. 4,610,868 issued Sep. 9, 1986) developed lipid matrix carriers which are described as globular structures of a hydrophobic compound and an amphiphatic compound with diameters from about 500 nm to about 100,000 nm. The hydrophobic compound can be liquid or solid. The preparation techniques, however, employ organic solvents and are thus associated with the problem of complete solvent removal.

So-called liposheres disclosed by Domb et al (U.S. patent application Ser. No. 435,546 lodged Nov. 13, 1989 and abandoned in favor of continuation application Ser. No. 07/770,706 filed Oct. 3, 1991, now U.S. Pat. No. 5,188,837; Int. Appl. No PCT/US90/06519 filed Nov. 8, 1990) are described as suspensions of solid, water-insoluble microspheres made of a solid hydrophobic core surrounded by a phospholipid layer. Liposheres are claimed to provide for the sustained release of entrapped substances controlled by the phospholipid layer. They can be prepared by a melt or by a solvent technique, the latter creating toxicological problems if the solvent is not completely removed.

A slow release composition of fat or wax and a biologically active protein, peptide or polypeptide suitable for parenteral administration to animals is disclosed in U.S. patent application Ser. No. 895,608 lodged Aug. 11, 1986 and now abandoned to Staber, Fishbein and Cady (EP-A-0 257 368). The systems are prepared by spray drying and consist of spherical particles in the micrometer size range up to 1.000 microns so that intravenous administration is not possible.

Problems with the formulation of water-insoluble or poorly water-soluble substances are not restricted to the parenteral route of administration. Thus, the peroral bioavailability of drugs is related to their solubility in the gastrointestinal tract (GIT), and it is generally found that poorly water-soluble drugs exhibit a low bioavailability. Moreover, the dissolution of drugs in the GIT is influenced by their wettability. Substances with apolar surfaces are scarcely wetted in media so that their dissolution rate is very slow.

In an attempt to improve the intestinal absorption of lipophilic drugs, Eldem et al (Pharm. Res. 8, 1991, 47–54) prepared lipid micropellets by spray-drying and spray-congealing processes. The micropellets are described as spherical particles with smooth surfaces. The lipids are, however, present in unstable polymorphic forms, and polymorphic phase transitions occur during storage so that the product properties are constantly changing (T. Eldem et al, Pharm. Res. 8, 1991, 178–184). Thus, constant product qualities cannot be assured.

Lipid nanopellets for peroral administration of poorly bioavailable drugs are disclosed in EP 0 167 825 of Aug. 8, 1990 to P. Speiser. The nanopellets represent drug-loaded fat particles solid at room temperature and small enough to be persorbed. Persorption is the transport of intact particles through the intestinal mucosa into the lymph and blood compartment. The lipid nanopellets are prepared by emulsifying molten lipids in an aqueous phase by high-speed stirring. After cooling to room temperature the pellets are dispersed by sonication.

OBJECT OF THE INVENTION

Considering the limitations of conventional drug carriers such as liposomes, lipid emulsions, nanoparticles and microspheres as outlined above there is an obvious demand for a carrier system for the controlled delivery of poorly water-soluble bioactive substances to circumvent the drawbacks of traditional systems particularly with regard to preparation, stability, toxicity and modification of biodistribution.

The present invention introduces a new type of carrier system characterized as non-spherically shaped particles composed of crystalline lipids, preferably triglycerides, and physiologically acceptable additives as well as a process for the manufacturing thereof. These carriers provide for the controlled delivery of poorly water-soluble substances such as drugs or other biological materials primarily by the parenteral but also by the peroral, nasal, pulmonary, rectal, dermal and buccal route of administration, and will hereinafter be referred to as solid lipid particles (SLPs).

SLPs are characterized as lipidic particles of a solid physical state in the micro- and predominantly in the nanometer size range. The shape of the particles is mainly anisometric which is a consequence of the matrix forming lipids present in a $\beta$-polymorphic modification (e.g. $\beta'$, $\beta_1$ $\beta_2$), and not in an amorphous or $\alpha$-crystalline state. The properties of the SLPs include: (1) biodegradability and non-toxicity; (2) the ability to incorporate poorly water-soluble substances; (3) improved chemical and physical stability; (4) the possibility to prepare a dry storage formulation; (5) control of release characteristics of incorporated substances; and (6) modified surface characteristics. As a result of these properties SLPs overcome many of the problems encountered with conventional drug carrier systems.

The present invention is supposed to bring about the following advantages as derived from the characteristics of the SLPs described above:

(1) SLPs can be prepared of biodegradable, pharmacologically acceptable compounds only and are, therefore, non-toxic. Additionally, the preparation of SLPs avoids the employment of organic solvents or any other potentially toxic additives, thus evading the contamination of the product with residual impurities.

(2) SLPs possess an enhanced chemical stability as compared with conventional lipid emulsions based on liquid triglyceride oils owing to the lower degree of unsaturated fatty acids of solid triglycerides. Moreover, SLPs exhibit a better physical stability due to the solid nature of the lipid matrix which is expectedly more resistant to coalescence than fluid emulsion droplets. Furthermore, the lipid matrix is present in a stable $\beta$-polymorphic modification (e.g. $\beta'$, $\beta_1$, $\beta_2$). Thus, the product properties will not change significantly during long-term storage due to polymorphic transformations.

(3) Suspensions of SLPs can be lyophilized by freeze-drying to provide a water-free storage system that exhibits a good long-term stability. The lyophilized powder can be redispersed in water, buffer or solutions of amino acids, carbohydrates and other infusion solutions directly before use or can be processed into other pharmaceutical formulations.

(4) Due to their lipophilic nature SLPs are suited for the solubilization of lipophilic and poorly water-soluble substances by entrapment into the lipid matrix. Compared to lipid emulsions SLPs are supposed to be less sensitive to the incorporation of drugs or other bioactive materials due to their solid nature. Drugs or other bioactive materials diffusing into the emulsifier film or recrystallizing close to the surface perturb the stabilizing film of emulsion droplets, increasing the risk of film rupture followed by coalescence. In contrast, film elasticity and film viscosity are of minor importance in the case of solid suspension particles since they cannot coalesce because of the rigid nature of the lipid.

(5) Drug release from the lipid carrier can be controlled for example by the composition of the lipid matrix by the choice of stabilizing agents as well as by the size of SLPs. Drug leakage is hindered by the solid state of the carrier due to the restricted drug diffusion.

(6) Drugs or bioactive substances exhibiting a short half-life due to enzymatic or hydrolytic degradation can be protected from rapid decomposition by incorporation within the lipid carrier since the hydrophobic matrix prevents the access of water to the incorporated drug on storage as well as in body fluids.

(7) The incorporation into SLPs of drugs or other bioactive substances with a low bioavailability due to poor solubility in the gastrointestinal tract (GIT) can enhance the bioavailability of such substances because these are solubilized in the biodegradable lipid matrix and are thus present in the dissolved state.

(8) Due to the anisometrical shape of SLPs the specific surface area is larger than that of spherical particles of the same volume. Substances with a low peroral bioavailability can be absorbed faster and to a higher degree in the GIT when they are incorporated in anisometrical SLPs than in spherical lipid particles of the same volume, due to the larger surface area of SLPs since the potential site of action for lipolytic enzymes is larger.

(9) The surface characteristics of SLPs can be modified by variation of the lipid composition, use of different stabilizers, exchange of surfactants and/or adsorption of polymeric compounds. The modification of surface characteristics brings about the possibility to modify the in vivo distribution of the carrier and the incorporated substance. In case of intravenous administration this implies a modified uptake by the RES with the potential for drug targeting.

(10) Due to the submicron particle size of SLPs there is no risk of embolism by parenteral administration. Since SLPs can be prepared down to a particle size of about 50 nm, they possess the opportunity of extravasation through fenestrations of the endothelial wall. Thereby, drugs can be targeted to extravascular sites such as the bone marrow, for example.

Furthermore, the present invention introduces a new type of delivery system for the parenteral, peroral, nasal, pulmonary, rectal, dermal and buccal administration of drugs or other bioactive substances as well as the process for the manufacturing thereof. These formulations are suspensions of particles formed by bioactive substances with modified surface characteristics and/or a reduced particle size as compared to the powdered substance, and will hereinafter be referred to as particles of bioactive agents (PBAs). The preparation of PBAs can avoid the employment of any toxicologically active additives such as organic solvents or toxic monomers, and can be accomplished by easy-to-handle techniques.

PBAs can be used in the following fields of application:
a) as a parenteral delivery system with modified biodistribution for sparingly water-soluble bioactive substances without the need of a carrier vehicle;
b) as a delivery system according to a) for peroral, nasal, pulmonary, rectal, dermal and buccal administration;
c) as a formulation for the peroral administration of drugs with a poor bioavailability due to a low dissolution rate in the gastrointestinal tract;
d) as a delivery system for use in agricultural applications;
e) the lyophilizate of formulations a) to d) as a reconstitutable powder with an enhanced stability on storage.

Owing to the special characteristics of the present invention PBAs are supposed to bring about the following advantages over conventional pharmaceutical delivery systems:

1) The formulation of poorly water-soluble drugs or other bioactive substances as micron and submicron particles avoids the need of a carrier system for their parenteral application, thereby circumventing the disadvantages of conventional drug carriers like liposomes, lipid emulsions, nanoparticles and microspheres.
2) PBAs can be prepared by easy-to-handle techniques in a reproducible way. There are no problems to foresee for the scaling up of the manufacturing process.
3) Since the particles consist of the pure bioactive compound with only small amounts of stabilizers the drug-load capacity of the drug particles is high.
4) The release of drugs or other bioactive compounds from the formulation can be controlled by the choice of amphiphatic compounds employed to stabilize the particles.
5) The preparation of PBAs can avoid the use of toxicologically active additives.
6) A water-free storage system with enhanced stability can be produced, for example by freeze-drying of the PBA dispersions.
7) The surface characteristics of PBAs can be modified by the choice of amphiphatic compounds used as stabilizers as well as by the attachment of so-called homing devices for the targeting of drugs, for example monoclonal antibodies or carbohydrate moieties. The surface modifications give rise to a modified bioavailability and biodistribution with regard to the extent and rate of absorption, the circulation time, the site of action and the way of disposition of the bioactive substance. The modification of surface characteristics also provides the opportunity to avoid or at least to reduce the uptake of intravenously administered particles by cells of the RES.
8) Since the particles can be prepared with a size below 100 nm to 200 nm they possess the opportunity for extravasation by fenestrations of the endothelial wall. Thereby, drugs can be targeted to extravascular sites such as the bone-marrow, for example.
9) A reduction in particle size to the nanometer size range generally not achievable by milling or grinding leads to an enormous increase of the specific surface area of the particles. Since the peroral bioavailability of drugs or other bioactive substances is related to the specific surface area via the dissolution rate of the substance in the gastrointestinal tract the submicron sized particles give rise to an enhanced bioavailability of drugs poorly soluble in the GIT.
10) Hydrophobic substances can be formulated as PBAs with hydrophilic surfaces. Hydrophilic surfaces provide for a good wettability of the particles, for example in the GIT, facilitating dissolution of the compound. Thus, the bioavailability can be increased.
11) The process of manufacturing of PBAs involves inexpensive easy-to-handle techniques only and provides a product which is safe to handle. Since the particles are present in a liquid dispersion there is no risk of dust explosions, cross-contamination or inhalation of bioactive substances as often encountered with the production of extremely fine powders.

DESCRIPTION OF THE INVENTION

Figure 1:
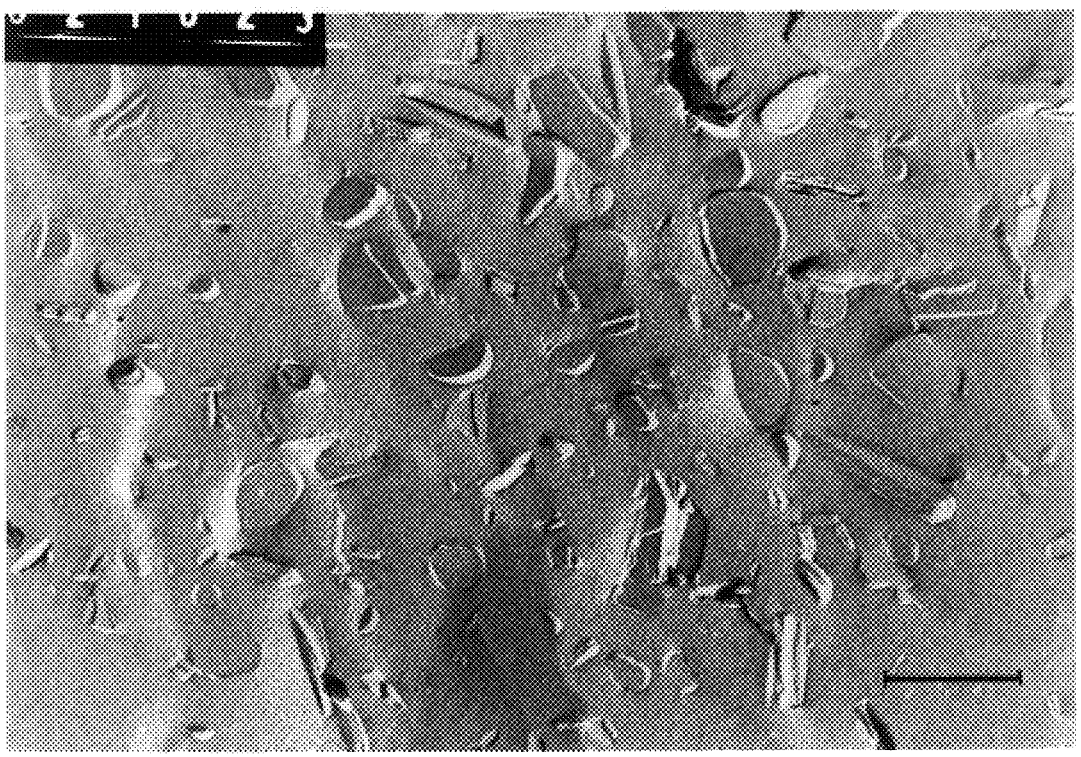
FIG. 1 is a transmission electron micrograph of a freeze-fractured specimen of tripalmitate SLPs.

The present invention relates to suspensions of micron and submicron particles of biodegradable lipids solid at room temperature (solid lipid particles, SLPs), to suspensions of particles of meltable bioactive substances (PBAs), to lyophilizates thereof and to methods for the manufacturing thereof.

Solid lipid particles (SLPs) are of predominantly anisometrical shape which is a consequence of the lipid matrix being present in a β-polymorphic modification (e.g. β', $β_1$, $β_2$) or in a polymorphic state analogous to that of β-crystals of triglycerides and not in an amorphous or α-crystalline-like state. SLPs can be used as carrier systems primarily for the parenteral but also for the peroral, nasal, pulmonary, rectal, dermal and buccal administration of poorly water-soluble substances such as drugs or other biologically active materials. The application of SLPs is, however, not restricted to the administration of pharmaceuticals to humans or animals. SLPs can also be used in cosmetic, food and agricultural products. SLPs are novel lipid structures with properties that overcome many of the problems associated with previously described carrier systems.

The matrix of SLPs is constituted by biocompatible hydrophobic materials which are solid at room temperature and have melting points ranging from approximately 30 to 120° C. The preferred matrix constituents are solid lipids (fats) such as mono-, di- and triglycerides of long-chain fatty acids; hydrogenated vegetable oils; fatty acids and their esters; fatty alcohols and their esters and ethers; natural or synthetic waxes such as beeswax and carnauba wax; wax alcohols and their esters, sterols such as cholesterol and its esters, hard paraffins, as well as mixtures thereof. The carrier material must be compatible with the agent to be incorporated.

Lipids are known to exhibit a pronounced polymorphism. This can be defined as the ability to reveal different unit cell structures in crystal, originating from a variety of molecular conformations and molecular packings. Depending on the conditions, glycerides, for example, may crystallize in three different polymorphic forms termed alpha (α), beta prime (β') and beta (β) according to the classification of Larsson (K. Larsson, 1966, Acta Chem. Scand. 20, 2255–2260). These polymorphic modifications characterized by a particular carbon chain packing may differ significantly in their properties such as solubility, melting point and thermal stability. Transformations take place from α to β' to β, the transition being monotropic. The β-form is the thermodynamically most stable polymorph, whereas α is the least stable and will transform more or less rapidly into the more stable polymorphs β' and β, depending on the thermal conditions. This transformation is accompanied by a change of physicochemical properties.

In the described suspensions of SLPs the lipid matrix is predominantly present in a stable polymorphic modification. Although on cooling, the dispersed melt metastable polymorphs such as the α-form may occur intermediately a stable polymorph is formed within several hours or days after preparation of the dispersions.

The suspensions of SLPs can be stabilized by amphiphatic compounds such as ionic and non-ionic surfactants. Suitable stabilizers include but are not limited to the following examples: naturally occurring as well as synthetic phospholipids, their hydrogenated derivatives and mixtures thereof, sphingolipids and glycosphingolipids; physiological bile salts such as sodium cholate, sodium dehydrocholate, sodium deoxycholate, sodium glycocholate and sodium taurocholate; saturated and unsaturated fatty acids or fatty alcohols; ethoxylated fatty acids or fatty alcohols and their esters and ethers; alkylaryl-polyether alcohols such as tyloxapol; esters and ethers of sugars or sugar alcohols with fatty acids or fatty alcohols; acetylated or ethoxylated mono- and diglycerides; synthetic biodegradable polymers like block co-polymers of polyoxyethylene and polyoxypropyleneoxide; ethoxylated sorbitanesters or sorbitanethers; amino acids, polypeptides and proteins such as gelatine and albumin; or a combination of two or more of the above mentioned.

The aqueous phase in which the SLPs are dispersed can contain water-soluble or dispersable stabilizers; isotonicity agents such as glycerol or xylitol; cryoprotectants such as sucrose, glucose, trehalose etc; electrolytes; buffers; antiflocculants such as sodium citrate, sodium pyrophosphate or sodium dodecylsulfate; preservatives.

Depending on the characteristics of the employed stabilizers the coexistence of other colloidal structures such as micelles and vesicles in suspensions of SLPs cannot be ruled out.

Substances particularly suitable for the entrapment into SLPs are drugs or other bioactive compounds which are poorly water-soluble, show a low bioavailability, are badly absorbed from the intestine, and/or will be rapidly degraded in biological environment by chemical or enzymatical processes, as well as low-specific active substances which are highly toxic at non-target sites. In case it is desired to incorporate a relatively water-soluble compound into SLPs it is necessary to decrease the water-solubility of this compound, which can be achieved for example by using a water-insoluble derivative of the compound such as an acid or base, a complex, or a lipophilic precursor.

Drugs or bioactive agents particularly suited for incorporation into SLPs are antibiotics such as fosfomycin, fosmidomycin and rifapentin; antihypertensives such as minoxidil, dihydroergotoxine and endralazine; antihypotensives such as dihydroergotamine; systemic antimycotics such as ketoconazole and griseofulvin; antiphlogistics such as indomethacin, diclofenac, ibuprofen, ketoprofen and pirprofen; antiviral agents such as aciclovir, vidarabin and immunoglobulines; ACE inhibitors such as captopril and enalapril; betablockers such as propranolol, atenolol, metoprolol, pindolol, oxprenolol and labetalol; bronchodilators such as ipratropiumbromide and sobrerol; calcium antagonists such as diltiazem, flunarizin, verapamil, nifedipin, nimodipin and nitrendipin; cardiac glycosides such as digitoxin, digoxin, methyldigoxin and acetyidigoxin; cephalosporins such as ceftizoxim, cefalexin, cefalotin and cefotaxim; cytostatics such as chlormethin, cyclophosphamid, chlorambucil, cytarabin, vincristin, mitomycin C, doxorubicin, bleomycin, cisplatin, taxol, penclomedine and estramustin; hypnotics such as flurazepam, nitrazepam and lorazepam; psychotropic drugs such as oxazepam, diazepam and bromazepam; steroid hormones such as cortisone, hydrocortisone, prednisone, prednisolone, dexamethasone, progesterone, pregnanolone, testosterone and testosteroneundecanoat; vasodilators such as molsidomin, hydralazin and dihydralazin; cerebral vasodilators such as dihydroergotoxin, cidonicat and vincamin; lipophilic vitamins such as vitamins A, D, E, K and their derivates.

The bioactive substances can be located in the core of SLPs where they are dissolved, solubilized or dispersed in the matrix, and/or in the stabilizer layer(s) surrounding the particle matrix, and/or can be adsorbed to the surface of SLPs. The bioactive substances can be dissolved or crystalline or amorphous or a mixture of these crystallographic states.

SLPs can be prepared by an emulsification process which exhibits certain similarities to the preparation of lipid(oil)-in-water emulsions but is mainly characterized by its basic differences as will be outlined below. The process is described as follows:

(1) The solid lipid or the mixture of lipids is melted.

(2) The stabilizers are added either to the lipid and to the dispersion medium or to the dispersion medium only, depending on their physicochemical characteristics. The choice of stabilizers and the admixture regime are not comparable with those applied for lipid (oil)-in-water emulsions, which is evident from the below examples. Stabilizers may also be added or exchanged after homogenization, for example by adsorption of polymers or by dialysis of water-soluble surfactants.

(3) Drugs or other bioactive substances to be incorporated into the SLPs may be melted together with the lipids if the physicochemical characteristics of the substance permit, or may be dissolved, solubilized or dispersed in the lipid melt before homogenization.

(4) The dispersion medium is heated to the temperature of the melt before mixing and may contain for example stabilizers, isotonicity agents, buffering substances, cryoprotectants and/or preservatives.

(5) The melted lipid compounds are emulsified in the dispersion medium, preferably by high pressure homogenization, but emulsification is also possible by sonication, high speed stirring, vortexing and vigorous hand shaking. The way of homogenization determines the particle size of the SLPs.

The basic differences to the preparation of lipid-in-water emulsions beside the choice and admixture regime of the stabilizers are related to the following steps:

(6) After homogenization the dispersion can be sterilized by standard techniques such as autoclaving or filtration through a 0.2 $\mu$m sterile filter provided the particles are small enough not to be retained by the filter. These steps have to be performed before the system is cooled below the recrystallization temperature. Moreover, contaminations which could lead to heterogenous nucleation should be avoided. It is therefore advisable to remove particulate contaminations from the dispersions by filtration prior to cooling below the recrystallization temperature. The pore size of the filter should be chosen sufficiently large so as not to retain the lipid particles.

(7) The dispersions are allowed to stand to cool off at room temperature forming SLPs by recrystallization of the dispersed lipids. During cooling the dispersion may be agitated by a magnetic stirrer for example.

(8) In a subsequent step the dispersion medium is reduced in volume for example by evaporation or it can be removed by standard techniques such as filtration, ultrafiltration or freeze-drying, thus yielding a water-free storage system which can be reconstituted prior to use. The lyophilized powder can also be processed into other pharmaceutical, cosmetic, food or agricultural formulations such as powders, tablets, capsules etc.

Figure 2A:
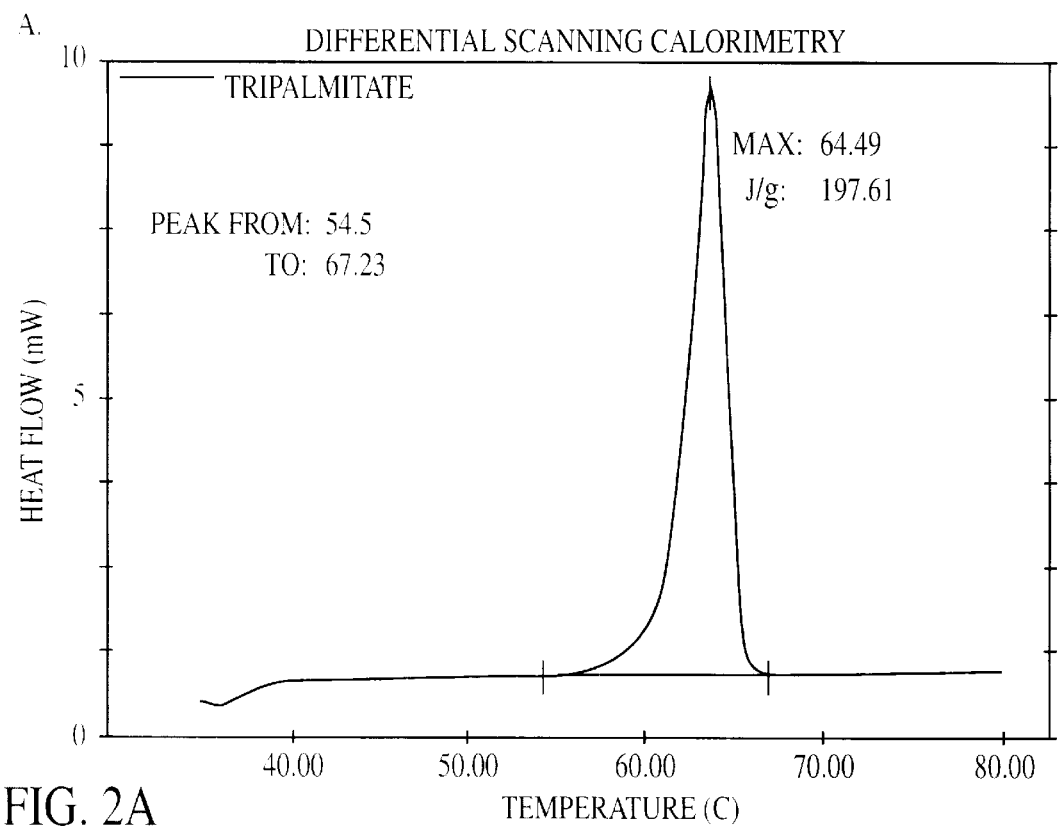
FIG. 2A is a differential scanning calorimetric thermogram of tripalmitate.
Figure 2B:
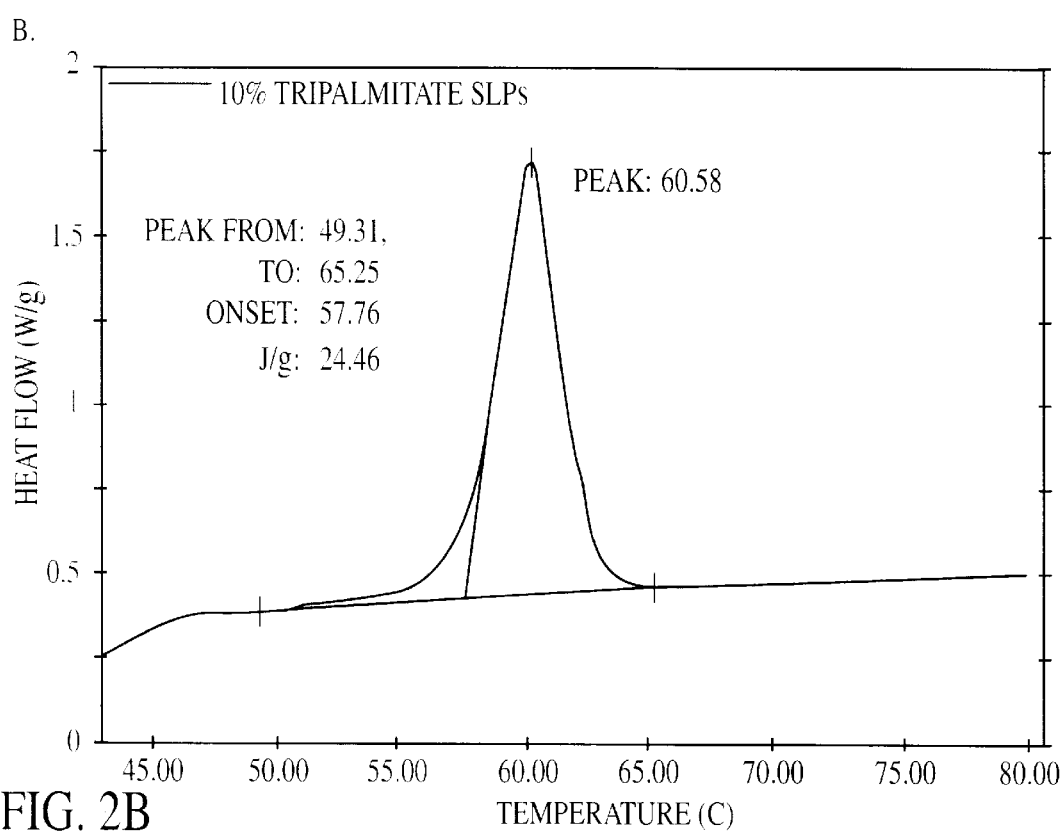
FIG. 2B is a differential scanning calorimetric thermogram of 10% tripalmitate SLPs.
Figure 3:
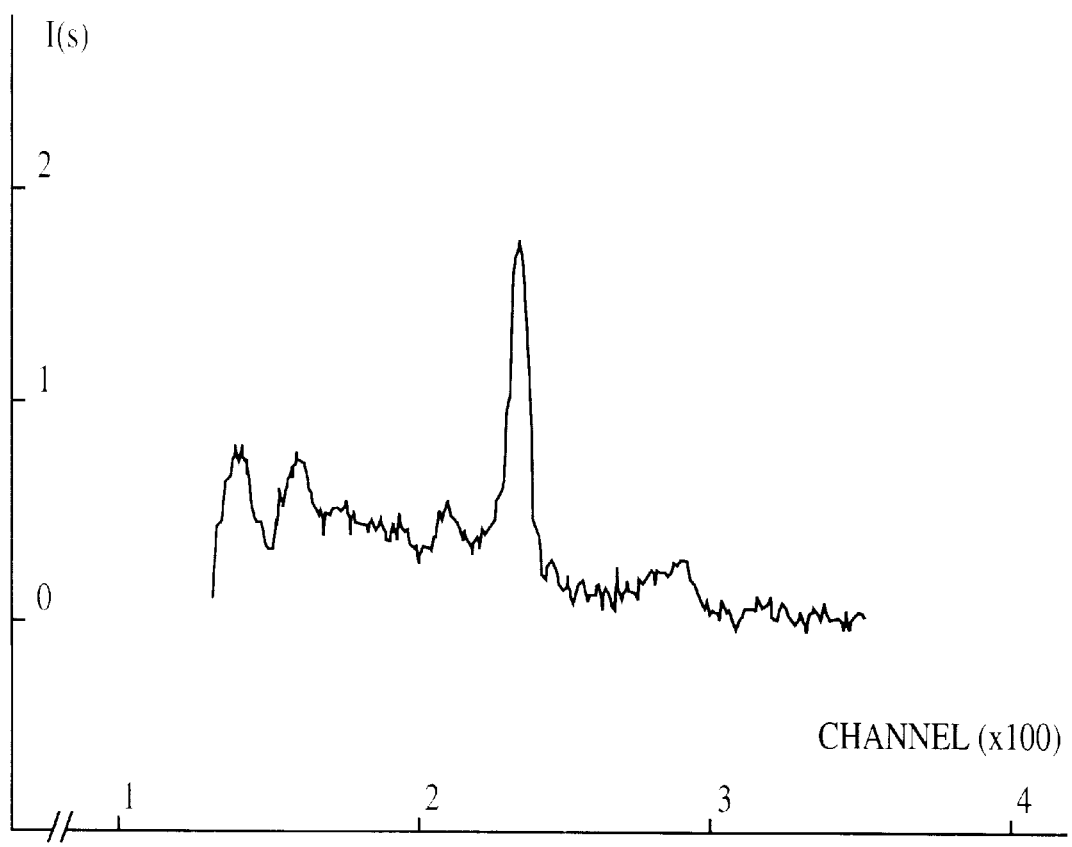
FIG. 3 is wide-angle X-ray diffraction of SLPs.

SLPs are typically solid particles of anisometrical shape as demonstrated by FIG. 1 which shows a transmission electron micrograph of a freeze-fractured specimen of the SLPs of Example 1. The anisometrical particle shape results from crystallization of the lipid matrix in the $\beta$-polymorphic form. Solidification of the amorphous fat or crystallization of the unstable $\alpha$-polymorph generally reveals spherical particles. The presence of the stable $\beta$-form could be detected by differential scanning calorimetry (FIG. 2) and synchrotron radiation wide-angle X-ray diffraction (FIG. 3).

The particle size of SLPs depends on the type and amount of emulsifier and on the emulsification technique and conditions (see below). The resolidification of the molten lipids prior to homogenization should be avoided because size reduction by homogenization is substantially impeded if the particles are solid during this step. To ensure that the molten lipids do not solidify prior to homogenization, i e before smaller particles can be formed, the dispersion medium is heated to approximately the same temperature as the melt before the two phases are mixed so that the melt will not be cooled down by the addition of the dispersion medium.

SLPs in the nanometer size range are obtained by high-pressure homogenization. The particles show a relatively narrow particle size distribution with mean particle sizes by number of approximately 50–300 nm as determined by photon correlation spectroscopy (PCS). The dispersions of SLPs are stable on storage for more than 18 months. Thus, the long-term stability is similar to that of submicron o/w emulsions used for parenteral nutrition. Long-term stability data of other solid lipid-based carrier dispersions described in the patent literature such as liposheres (A. Domb et al, Int. Appl. No PCT/US90/06519 filed Nov. 8, 1990) and lipid nanopellets (P. Speiser, Eur. Pat. No 0167825 issued Aug. 8, 1990) could not be found. Domb describes phospholipid stabilized tristearate liposheres with a seven day stability as "exceptionally stable".

It turned out that the stabilization of SLP suspensions requires the presence of a highly mobile stabilizing agent in the dispersion medium in such a way that the amount of highly mobile stabilizers in the dispersion medium is, after emulsification, sufficient to stabilize newly created surfaces during recrystallization (see below). Bile salts, especially in combination with nonelectrolytic compounds such as glycerol in concentrations used to achieve blood isotony, have proved to be very efficient in this respect. SLPs stabilized by phospholipids alone, or in combination with nonelectrolytic compounds such as glycerol in concentrations used to achieve blood isotony, tend to form semi-solid ointment-like gels as shown on the transmission electron micrograph of FIG. 4, whereas the addition of sodium glycocholate to the aqueous phase prevents this gel formation (B. Siekmann and K. Westesen, 1992, Pharm. Pharmacol. Lett. 1, 123–126).

A molar phospholipid to bile salt ratio between 2:1 and 4:1 turned out to be most effective regarding the initial stabilization during homogenization as well as the long-term storage stability of SLP dispersions. These phospholipid/bile salt ratios are above the ratio of formation of mixed micelles and coincide with a swollen lamellar phase of mixed lecithin/bile salt layers in the ternary phase diagram of the system lecithin/bile salt/water. Data therefore suggest that stabilization is most effective if the bile salt is not bound to mixed micelles and that during stabilization of SLPs the bile salt molecules are inserted in the phospholipid layer on the surface of the particles.

SLPs can also be sterically stabilized by nonionic surfactants. Steric stabilization of SLPs requires, however, a relatively high amount of surfactants with lipid/surfactant ratios up to 1:1. It can be observed in general that the stability of SLPs decreases with increasing lipid/surfactant ratio.

The amount of emulsifier required for surface stabilization of the dispersed particles is higher than in conventional lipid emulsions, for example such as used in parenteral nutrition. This effect can be attributed to the crystallization of the molten lipids after homogenization. Since the lipids typically do not recrystallize or exist (on storage) in the form of ideal spheres but as anisometric particles there is a large increase in surface area as compared to the droplets of the emulsified molten lipids or of conventional lipid emulsions, respectively. The additional surfaces newly generated during recrystallization or polymorphic transitions of the dispersed lipids need to be stabilized immediately on formation to avoid particle aggregation. Therefore, the preparation of stable SLP dispersions requires the presence of a reservoir of stabilizing agents after emulsification.

The choice of stabilizers cannot be deduced from compositions and stabilization mechanisms for oil-in-water emulsions but is dependent on the existence of highly mobile stabilizers due to the formation mechanism of the anisometrical particles. In colloid and surface science "highly mobile" generally refers to free diffusion in the dispersion medium at a high diffusion velocity. With regard to the stabilization of colloidal solid lipid particles the diffusion velocity should be sufficiently high to reach freshly created particle surfaces (especially during re-crystallization of the lipid) before particle aggregation can take place, in order to exert a stabilizing action at the lipid/water interface to prevent particle aggregation. Sufficiently high diffusional velocities are typically observed with substances which do not form a separate phase in the dispersion medium according to the phase rule set up by Gibbs. Highly mobile stabilizers can be of ionic or nonionic nature. Typically, these stabilizers dissolve molecularly in the dispersion medium and/or form micelles. Micelles are known to be highly dynamic structures characterized by a fast exchange of molecules between micellar aggregates and the dispersion medium. The monomers in the dispersion medium are immediately available for surface stabilization. In contrast, stabilizing agents that tend to form a separate phase in the dispersion medium are not sufficiently mobile to stabilize freshly created surfaces before particle aggregation can take place. These stabilizers are therefore not suitable as sole stabilizers of SLP dispersions. Phospholipids are an example of stabilizing agents that form a separate phase in the dispersion medium. It is well known that phospholipids form closed lamellar structures, so called vesicles, in aqueous media, and that the exchange rate of phospholipid molecules between vesicles and the aqueous phase is extremely small compared to that of micelles. Phospholipid molecules are therefore bound in vesicular structures and are not immediately available to stabilize newly created surfaces during recrystallization of the lipid particles. Consequently, phospholipids alone, although suitable as effective stabilizers of lipid emulsions, cannot efficiently stabilize SLP suspensions as is evident from Examples 5 and 13. In fact, preparing SLPs with a standard composition of lipid emulsions, for example 10% fat and 1.2% phospholipids, results in unstable SLP dispersions. Even higher concentrations of phospholipids such as 20% or 60% lecithin related to the fat phase are not sufficient to stabilize SLP dispersions as demonstrated in Example 5.

Although stated in the patent literature (e.g. Domb et al in U.S. application Ser. No. 435,546 filed Nov. 13, 1989 and abandoned in favor of continuation application Ser. No. 07/770,706 filed Oct. 3, 1991, now U.S. Pat. No. 5,188,837, and Int. Appl. No PCT/US90/0651 9 filed Nov. 8, 1990), fine suspensions of solid lipids are not equivalent to submicron lipid emulsions in that respect that the inner phase is only replaced by solid fats instead of liquid ones. The physicochemical properties of lipid suspensions such as SLPs differ substantially from that of lipid emulsions. As a consequence of these differences lipid suspensions cannot be prepared and treated analogously to lipid emulsions. One basic difference of SLPs is their much larger particle surface area as outlined above so that SLPs require a higher amount of surfactants which additionally need to be highly mobile to immediately stabilize the new surfaces created when the molten lipid recrystallizes or transforms into the stable β-polymorph. The second basic difference is that once SLPs are formed by recrystallization of the molten lipid any renewed melting of the small particles may result in an instability of the dispersions if there is no excess of mobile stabilizer in the aqueous phase which is not adsorbed to particle surfaces where it is immobilized. A further requirement for physicochemical stability of SLPs in contrast to oil-in-water emulsions is the absence of particulate impurities which could promote heterogenous nucleation. It is therefore advisable to remove particulate contaminations from the dispersions by filtration prior to cooling below the recrystallization temperature. Moreover, non-electrolytic compounds used to achieve blood isotony such as glycerol turned out to promote the stability of SLP dispersions.

The present invention also relates to suspensions of particles of bioactive agents (PBAs). Sparingly water-soluble substances such as drugs, insecticides, fungicides, pesticides, herbicides, fertilizers, nutrients, cosmetics etc which are meltable in the temperature range from approximately 30 to 120° C. can be formulated as PBAs by a procedure similar to the preparation of SLPs as described above. The matrix of PBAs is constituted by the bioactive agent itself.

PBAs present a novel type of delivery system and can be characterized as predominantly submicron and/or micron particles of bioactive agents suspended in an aqueous media stabilized by amphiphatic compounds. PBAs possess modified surface characteristics which can be controlled by the choice of amphiphiles and/or a reduced particle size of the matrix constituting compound as compared to the powdered substance. These characteristics give rise to a modified biodistribution and bioavailability of the formulated drugs or other bioactive substances which implies a modification of the extent and rate of dissolution and absorption, the circulation time, the site of action and the way of disposition of the drug or other bioactive substance. The physicochemical properties of PBAs depend strongly on the characteristics of the bioactive agent of which they are formulated, on the type and amount of stabilizing agents as well as on the way of emulsification. Suspensions and lyophilizates of PBAs can be used for the peroral, nasal, pulmonary, rectal, dermal, buccal and, depending on the particle size, also for the parenteral administration of poorly water-soluble drugs or other biologically active compounds. Moreover, PBAs can also be employed in cosmetic, food and agricultural products, in particular for the formulation of poorly water-soluble herbicides and pesticides.

The matrix of PBAs is constituted by practically insoluble or sparingly water-soluble agents with melting points preferably below 100° C. or the melting points of which can be decreased to below 100° C. by the addition of certain adjuvants. Substances particularly suitable for the formulation as PBAs are drugs or other bioactive materials which are poorly water-soluble, show a low bioavailability and/or are badly absorbed from the intestinum. Examples of such substances comprise but are not limited to:

Anesthetics and narcotics such as butanilicaine, fomocaine, isobutambene, lidocaine, risocaine, prilocaine, pseudococaine, tetracaine, trimecaine, tropacocaine and etomidate; anticholinergics such as metixen and profenamine; antidepressives, psychostimulants and neuroleptics such as alimenazine, binedaline, perazine, chlorpromazine, fenpentadiol, fenanisol, fluanisol, mebenazine, methylphenidate, thioridazine, toloxaton and trimipramine; antiepileptics such as dimethadion and nicethamide; antimycotics such as butoconazole, chlorphenesin, etisazole, exalamid, pecilocine and miconazole; antiphlogistics such as butibufen and ibuprofen; bronchodilators such as bamifylline; cardiovascular drugs such as alprenolol, butobendine, cloridazole, hexobendine, nicofibrate, penbutolol, pirmenol, prenylamine, procaine amide, propatylnitrate, suloctidil, toliprolol, xibendol and viquidile; cytostatics such as asperline, chlorambucile, chlornaphhazine, mitotane, estramustine, taxol, penclomedine and trofosfamide; hyperemic drugs such as capsaicine and methylnicotinate; lipid reducers such as nicoclonate, oxprenolol, pirifibrate, simfibrate and thiadenol; spasmolytics such as aminopromazine, caronerine, difemerine, fencarbamide, tiropramide and moxaverine; testosterone derivates such as testosterone enantate and testosterone-(4-methylpentanoate); tranquilizers such as azaperone and buramate; virustatics such as arildon; vitamin A derivates such as retinol, retinol acetate and retinol palmitate; vitamin E derivates such as tocopherol acetate, tocopherol succinate and tocopherol nicotinate; menadione; cholecalciferol; insecticides, pesticides and herbicides such as acephate, cyfluthrin, azinphosphomethyl, cypermethrine, substituted phenyl thiophosphates, fenclophos, permethrine, piperonal, tetramethrine and trifluraline.

As with SLPs, suspensions of PBAs can be stabilized by amphiphatic compounds. Principally the same ionic and nonionic surfactants which may be employed for the stabilization of SLPs are also suitable for the preparation of PBA suspensions. The choice of stabilizing agents depends on the physicochemical properties of both the bioactive substance and the dispersion medium as well as on the desired surface characteristics of the particles.

The aqueous phase in which the PBAs are dispersed should contain water-soluble (or dispersable) stabilizers; isotonicity agents such as glycerol or xylitol; cryoprotectants such as sucrose, glucose, trehalose etc; electrolytes; buffers; antiflocculants such as sodium citrate, sodium pyrophosphate or sodium dodecylsulfate; preservatives. Although water is the preferred dispersion medium the invention is, however, not restricted to aqueous dispersions alone but can be extended to any other pharmacologically acceptable liquid such as ethanol, propylene glycol and methyl-isobutyl-ketone, or a mixture thereof.

Depending on the characteristics of the employed stabilizers the coexistence of other colloidal structures such as micelles and vesicles in suspensions of PBAs cannot be ruled out.

Suspensions of PBAs are typically prepared by an emulsification process similar to that of SLPs. The molten drug or bioactive substance or a mixture of such compounds is emulsified in a pharmacologically acceptable liquid immiscible with the melt, preferably by high-pressure homogenization. Emulsification is also possible by sonication, high-speed stirring, vortexing and vigorous hand shaking. The liquid is heated to the temperature of the melt before mixing and may contain for example isotonicity agents, buffering substances, cryoprotectants and/or preservatives.

The stabilizing amphiphatic compounds are added either to the melt and to the liquid or to the liquid only, depending on their physicochemical characteristics. Stabilizers may also be added or exchanged after homogenization, for example by the adsorption of polymers or by dialysis.

The PBAs manufactured according to the above described process can be categorized in two distinguishable groups.

The PBAs of the first group are characterized in that they are water-insoluble at the temperature of emulsion preparation and will not be solubilized by the excess of stabilizers or form micelles by themselves, the particle size of PBAs remaining unchanged before and after cooling to room temperature.

The PBAs of the second group are characterized in that they are partly water-soluble at the temperature of emulsion preparation and/or are able to form mixed micelles by the excess of stabilizers and/or form micelles by themselves, leading to an increase of particle size after cooling to room temperature due to, for example, crystal growth and/or precipitation of dissolved bioactive agent from the supersaturated solution and/or due to mass transport from smaller to larger particles, for example in micelles and/or by processes such as Ostwald ripening.

In a subsequent step the liquid phase can be removed by freeze-drying, for example, producing a reconstitutable powder which can also be processed into other pharmaceutical formulations.

PBAs are finely dispersed particles consisting of a matrix of bioactive material surrounded by one or more layers rich in surfactant. The particle size and the size distribution as well as the particle shape and the surfactant coating depend on the properties and amounts of the matrix forming bioactive substances and the stabilizing agents, the ratio of bioactive material to amphiphatic compounds as well as on the way of emulsification.

EXAMPLES

Example 1

Method of preparation of tripalmitate SLPs

In a thermostatized vial 4.0 g tripalmitate (tripalmitin, 99% pure, Fluka) is heated to 75° C. to melt the lipid. In the lipid melt 0.48 g soy bean lecithin (Lipoid S 100, Lipoid KG) is dispersed by probe sonication (MSE Soniprep 150) until the dispersion appears optically clear. 0.16 g sodium glycocholate (glycocholic acid, sodium salt 99%, Sigma) and 4 mg thiomersal (Synopharm) is dissolved in 36 ml bidistilled water. The aqueous phase is heated to 75° C. and added to the lipid melt. A crude dispersion is produced by probe sonication for approximately 2 minutes. The crude dispersion is transferred to a thermostatized high-pressure homogenizer (APV Gaulin Micron Lab 40) and passed 5 times through the homogenizer at a pressure of 500 bar. Homogenization with this equipment is accomplished by extrusion through a small ring-shaped orifice. The homogenized dispersion is allowed to stand at room temperature to cool off. The dispersion reveals trace amounts of visible fat particles which are separated from the dispersion by filtering it through a 0.45 µm sterile filter.

The importance of the admixture of highly mobile surfactants such as bile salts with regard to the particle size distributon and the stability of SLP dispersions is demonstrated below, e.g. in Examples 2, 5 to 7 and 13 to 15.

Figure 5:
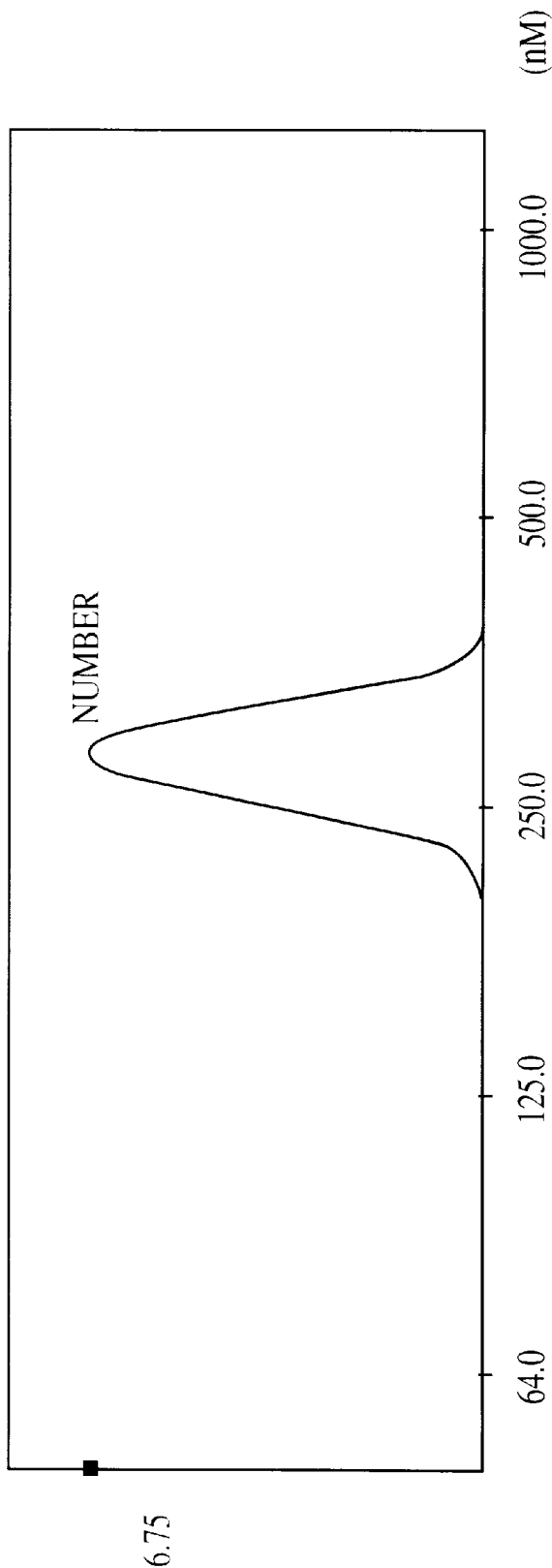
FIG. 5 is a PCS multiangle measurement of tripalmitate SLP dispersion.

The mean particle size after preparation (by number) of the tripalmitate SLPs determined by photon correlation spectroscopy (PCS, Malvern Zetasizer 3) is 205 nm. After 15 months of storage the particles show no visible signs of aggregation, creaming, sedimentation or phase separation. A PCS multiangle measurement (Malvern Zetasizer 3, detection at five different angles: 50, 70, 90, 110 and 130 degrees) reveals a monomodal particle size distribution (by number) with a peak at 250 nm (FIG. 5).

At temperatures below the melting point of the lipid matrix tripalmitate SLPs are predominantly anisometrical particles as demonstrated in FIG. 1 which is a transmission electron micrograph of a freeze-fractured specimen of the tripalmitate SLPs of Example 1. Before preparation of the specimen the sample is stored at room temperature for 5 months. The sample is freeze-fractured at 173 K in a freeze-fracture unit BAF 400 (Balzers AG, CH-Liechtenstein). Fast freezing is accomplished by slush into melting propane. Shadowing of the sample is performed with platinum/carbon (layer thickness 2 nm) at 45 degrees and with pure carbon at 90 degrees for replica preparation. Replica are cleaned with a 1:1 (v/v) chloroform/ethanol mixture. Replica on uncoated grids are viewed with an electron microscope EM 300 (Philips, D-Kassel).

In the anisometrical tripalmitate particles the glyceride is present in the stable β-crystalline polymorph as indicated by thermoanalytical investigations. FIG. 2A and FIG. 2B present a differential scanning calorimetric (DSC) thermogram of SLPs of Example 1 FIG. 2A and of pure tripalmitate in FIG. 2B. The samples are weighed accurately into standard aluminium pans. Thermograms are recorded from 20° C. to 90° C. at a scan rate of 10° C./minute on a Perkin Elmer calorimeter DSC-7. The detected transition peaks correspond to the melting of tripalmitate β-crystals. The melting point of tripalmitate SLPs is shifted to a lower temperature compared to that of pure tripalmitate due to the presence of phospholipids and due to the small crystallite size.

Example 2

Method of preparation of isotonic tripalmitate SLPs 7.0 g tripalmitate (tripalmitin, Fluka) is melted in a vial thermostatized at 75° C. 840 mg soy bean lecithin (Lipoid S 100, Lipoid KG) is dispersed in the tripalmitate melt as described in Example 1. The aqueous phase containing 1.575 g glycerol, 280 mg sodium glycocholate and 4 mg thiomersal is heated to 75° C. and added to the lipid melt to a weight of 70 g. A crude dispersion is produced by sonication for approximately 2 minutes. The crude dispersion is transferred to a thermostatized high-pressure homogenizer (APV Gaulin Micron Lab 40) and passed 10 times through the homogenizer at a pressure of 800 bar. The homogenized dispersion is allowed to stand at room temperature to cool off.

The mean particle size by number of the isotonic tripalmitate SLPs determined by PCS is 125.9 nm after preparation and 116.2 nm after 50 days of storage, i e there was practically no particle growth. The slight deviations of the values fall into the range of accuracy of the sizing method. The PCS particle size distribution is compared to that of the commercially available lipid emulsion for parenteral nutrition Intralipid™ in FIG. 6. Intralipid™ is composed of 10% soy bean oil, 1.2% fractionated phospholipids and 2.25% glycerol dispersed in water for injection. It can be observed that the particle size distribution of tripalmitate SLPs of Example 2 is significantly smaller and more narrow than that of Intralipid™. In contrast to Example 1 the addition of glycerol results in a noticeable difference in the particle size distribution. Whereas the SLP dispersion of Example 1 contains trace amounts of visible suspension particles after being cooled to room temperature from the hot emulsion no macroscopically visible suspension particles are observed in the dispersion of Example 2.

Investigations by synchrotron radiation wide-angle X-ray diffraction (FIG. 3) and differential scanning calorimetry reveal that the tripalmitate in SLPs is present in the stable β-polymorphic form at room temperature.

Example 3

Preparation of hard fat SLPs by microfluidization 3.0 g hard fat (Witepsol™ W35, Hüls AG) is melted in a thermostatized vial at 75° C. 1.8 g soy bean lecithin (Phospholipon 100, Natterman) is dispersed in the tripalmitate melt as described in Example 1. The aqueous phase containing 375 mg sodium glycocholate, 2.25 g glycerol and 10 mg thiomersal is heated to 75° C. and added to the lipid melt to a weight of 100 g. A crude dispersion is produced by ultra-turrax vortexing for approximately 2 minutes. The crude dispersion is transferred to a microfluidizer (Microfluidics Microfluidizer M-110T), a high-pressure homogenizer of the jet-stream principle which is immersed in a thermostatized water bath (70° C.). The dispersion is cycled through the microfluidizer for 10 minutes and allowed to stand at room temperature to cool off.

The mean particle size of hard fat SLPs after preparation is 45.9 nm as determined by PCS.

Figure 7:
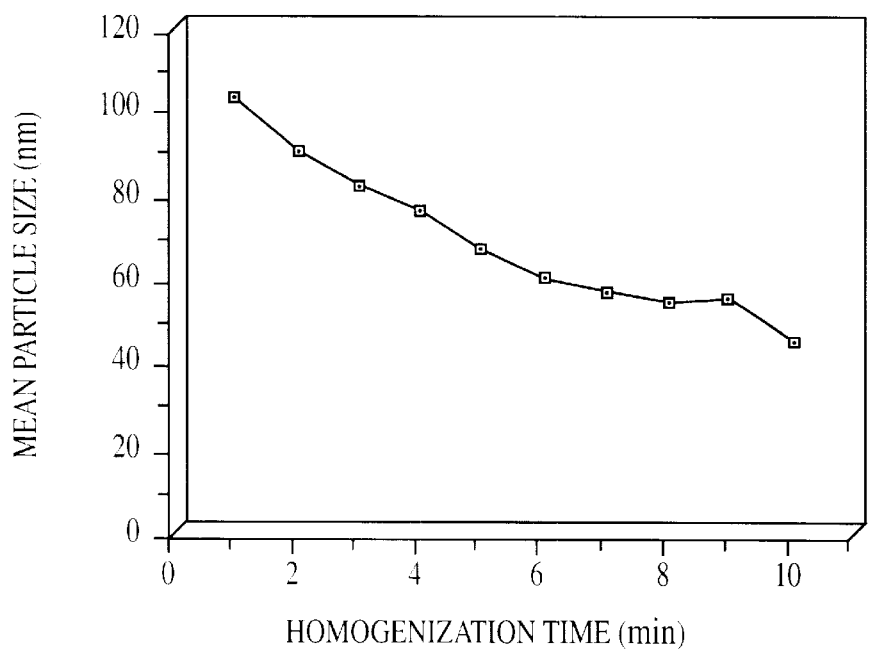
FIG. 7 shows the mean particle size of hard fat SLPs versus homogenization time.

During homogenization a sample for particle sizing is drawn each minute in order to monitor the time course of homogenization. FIG. 7 displays the mean particle size versus homogenization time. The mean particle diameter is decreasing with time and levels off at the end of homogenization.

Example 4

Long-term stability of hard fat SLPs prepared by microfluidization

Figure 8:
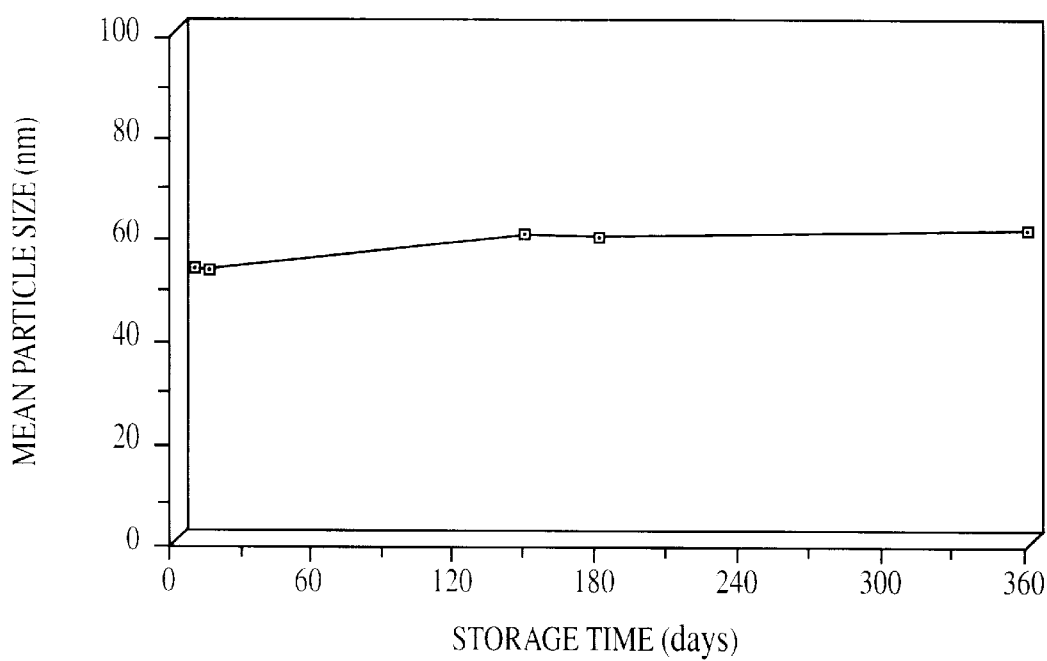
FIG. 8 shows the mean particle size of hard fat SLPs versus storage time.

The stability of hard fat SLPs is monitored over a period of one year. During this time the sample is stored in a refrigerator at approximately +4° C. After certain time intervals the particle size distribution of the sample is determined by PCS. FIG. 8 demonstrates that the mean particle size of hard fat SLPs is practically constant over the monitored period of one year.

Example 5

Preparation of unstable SLPs dispersions

In a thermostatized vial 4.0 g tripalmitate (Dynasan 116, Hüls AG) is heated to 75° C. to melt the lipid. In the lipid melt 0.48 g soy bean lecithin (Lipoid S 100, Lipoid KG) is dispersed by probe sonication (MSE Soniprep 150) until the dispersion appears optically clear. 4 mg thiomersal and 0.9 g glycerol is dissolved in 35.6 ml bidistilled water. The aqueous phase is heated to 75° C. and added to the lipid melt. A crude dispersion is produced by probe sonication for approximately 2 minutes. The crude dispersion is transferred to a thermostatized high-pressure homogenizer (APV Gaulin Micron Lab 40) and passed 5 times through the homogenizer at a pressure of 500 bar. The homogenized dispersion is allowed to stand at room temperature to cool off. On storage the SLP dispersion becomes a milky semi-solid, ointment-like gel.

3.0 g hard fat (Witepsol™ W35, Hüls AG) is melted in a thermostatized vial at 75° C. 1.8 g soy bean lecithin (Phospholipon 100, Natterman) is dispersed in the tripalmitate melt as described in Example 1. The aqueous phase containing 10 mg thiomersal is heated to 75° C. and added to the lipid melt to a weight of 100 g. A crude dispersion is produced by ultra-turrax vortexing for approximately 2 minutes. The crude dispersion is transferred to a microfluidizer (Microfluidics Microfluidizer M-110T) which is immersed in a thermostatized water bath (70° C.). The dispersion is cycled through the microfluidizer for 10 minutes and allowed to stand at room temperature to cool off. On storage the SLP dispersion becomes a turbid semi-solid, ointment-like gel. A transmission electron micrograph of this gel is presented in FIG. 4.

In a thermostatized vial 4.0 g tripalmitate (Dynasan 116, Hüls AG) is heated to 80° C. to melt the lipid. In the lipid melt 0.8 g of a soy bean lecithin mixture (Lipoid S 75, Lipoid KG) is dispersed by probe sonication (MSE Soniprep 150) until the dispersion appears optically clear. 4 mg thiomersal is dissolved in 35.6 ml bidistilled water. The aqueous phase is heated to 80° C. and added to the lipid melt. A crude dispersion is produced by probe sonication for approximately 2 minutes. The crude dispersion is transferred to a thermostatized high pressure homogenizer (APV Gaulin Micron Lab 40) and passed 5 times through the homogenizer at a pressure of 800 bar. The homogenized dispersion is filled in a glass vial and allowed to stand at room temperature to cool off. On cooling to room temperature the dispersion forms semi-solid looking fat aggregates on the wall of the glass vial. The dispersion gelatinizes when shear forces are applied, for example by passing it through a hypodermic syringe.

Obviously the use of phospholipids only as stabilizers, as found in commercial parenteral oil-in-water emulsions, does not yield stable systems in the case of SLP suspensions. Even the employment of phospholipids such as Lipoid S 75 which induces a considerably high negative net charge cannot provide a sufficient stabilization. Electrostatic repulsion alone cannot be the basic stabilization mechanism of SLPs as will be further outlined in Examples 6, 7 and 13.

Example 6

Preparation of tripalmitate SLPs sterically stabilized by tyloxapol

A series of tripalmitate SLP dispersions stabilized by tyloxapol (Eastman Kodak) are prepared with varying lipid/surfactant ratios. The SLP dispersions are manufactured according to the following procedure:

Tyloxapol is dissolved in heated bidistilled water while the temperature is held below the cloud point of tyloxapol (approximately 90–95° C.). The tyloxapol solution of a temperature of 80° C. is added to the molten tripalmitate or, respectively, tripalmitate/lecithin dispersion of the same temperature. A crude emulsion is prepared by probe sonication for approximately 2 minutes. Then the crude emulsion is passed 5 times through a high-pressure homogenizer at a pressure of 1200 bar. The homogenized dispersion is allowed to stand at room temperature to cool off. All dispersions contain 2.5% glycerol and 0.01% thiomersal.

Table 1 gives the composition of the prepared SLP dispersions and their mean particle size after preparation (by number) as determined by PCS. The asterix (*) in the particle size column indicates that the dispersions display a bimodal size distributon with particle sizes considerably larger than indicated by the mean particle size. It turns out that sterically stabilized SLP dispersions require a high amount of surfactant in order to obtain homogenously sized SLPs. In case of SLPs stabilized by tyloxapol and phospholipids the ratio of the surfactants needs to be optimized. In the present series a tyloxapol/lecithin ratio of at least 1:1 turned out to yield homogenously sized SLPs. With increasing ratio the mean particle size is decreasing. As with examples 1 to 3 the addition of a highly mobile surfactant which is able to form micelles is required to obtain stable dispersions. The high amount of surfactant is needed to create a reservoir of surfactant in the dispersion medium that can provide enough surfactant molecules at the moment when the molten lipids recrystallize and form anisometrical particles with a large specific surface area.

TABLE 1

SLP dispersions sterically stabilized by tyloxapol.

| Composition (w %) | | | Mean particle |
| --- | --- | --- | --- |
| TP | Tyl | PL | size (nm) |
| 10 | 2 | — | 138.0* |
| 10 | 4 | — | 84.9 |
| 10 | 0.7 | 2 | 487.4* |
| 10 | 1 | 2 | 207.4* |
| 10 | 2 | 2 | 102.8 |
| 10 | 4.5 | 3 | 60.9 |

Abbreviations: TP = tripalmitate, Tyl = tyloxapol, PL = phospholipids (Lipoid S 100).

Example 7

Preparation of tripalmitate SLPs sterically stabilized by poloxamers 1.2 g soy bean lecithin (Lipoid S 100, Lipoid KG) is dispersed in 4.0 g molten tripalmitate (Dynasan 116, Hüls AG) by probe sonication at a temperature of 80° C. 1.8 g poloxamer (Pluronic™ F68, BASF), 0.9 g glycerol and 4 mg thiomersal is dissolved in 32.1 g bidistilled water heated to 80° C. The heated solution is added to the lipid melt and a crude dispersion is prepared by 2 minutes probe sonication. The crude dispersion is transferred to a thermostatized high-pressure homogenizer (APV Gaulin Micron Lab 40) and passed 5 times through the homogenizer at a pressure of 1200 bar. The homogenized dispersion is allowed to stand at room temperature to cool off.

The poloxamer stabilized SLPs display a monomodal size distribution with a mean particle size (by number) after preparation of 77.9 nm determined by PCS. Due to the presence of an excess of highly mobile surfactant in the aqueous phase the system is stabilized on recrystallization of the molten lipids and a gelation as found with systems stabilized by phospholipids only does not occur.

Example 8

The influence of homogenization pressure on the mean particle size of SLPs

SLPs of the following composition are prepared at different homogenization pressures. The SLP dispersions are composed of 3% tripalmitate (Dynasan 116, Hüls AG), 1.5% tyloxapol, 1% soy bean lecithin (Lipoid S 100, Lipoid KG), 0.01% thiomersal and bidistilled water to 100% (by weight). The lecithin is dispersed in the molten tripalmitate (80° C.) by probe sonication until the dispersion appears optically clear. Tyloxapol is dissolved in warm water (80° C.) containing thiomersal. The SLP dispersions are prepared as described in Example 6.

Figure 9:
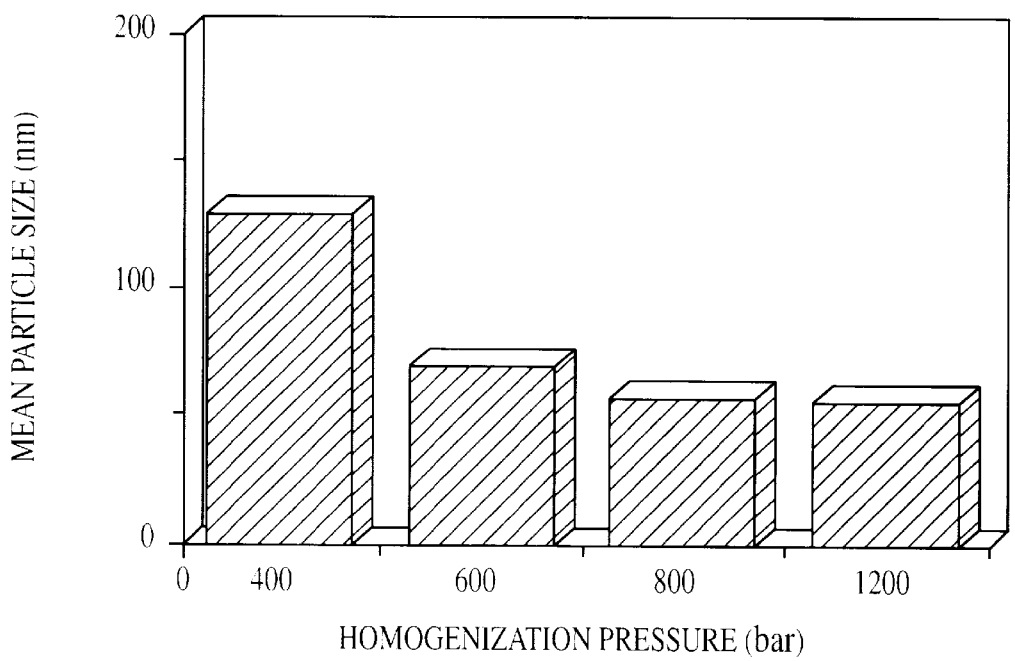
FIG. 9 shows the effect of homogenization pressure on the mean particle size of SLPs.

FIG. 9 displays the influence of homogenization pressure on the mean particle size of the SLPs. With increasing pressure the particle size is decreasing and the particle size distribution becomes more narrow.

Example 9

The influence of homogenization passes on the mean particle size of SLPs

Tripalmitate SLPs composed of 3% tripalmitate (Dynasan 116, Hüls AG), 1.5% tyloxapol, 1% soy bean lecithin (Lipoid S 100, Lipoid KG), 0.01% thiomersal and bidistilled water to 100% (by weight) is prepared at a pressure of 800 bar as described in Example 6. Samples for size measurements are taken from the dispersion after preparation of the crude emulsion and after each pass through the homogenizer.

Figure 10:
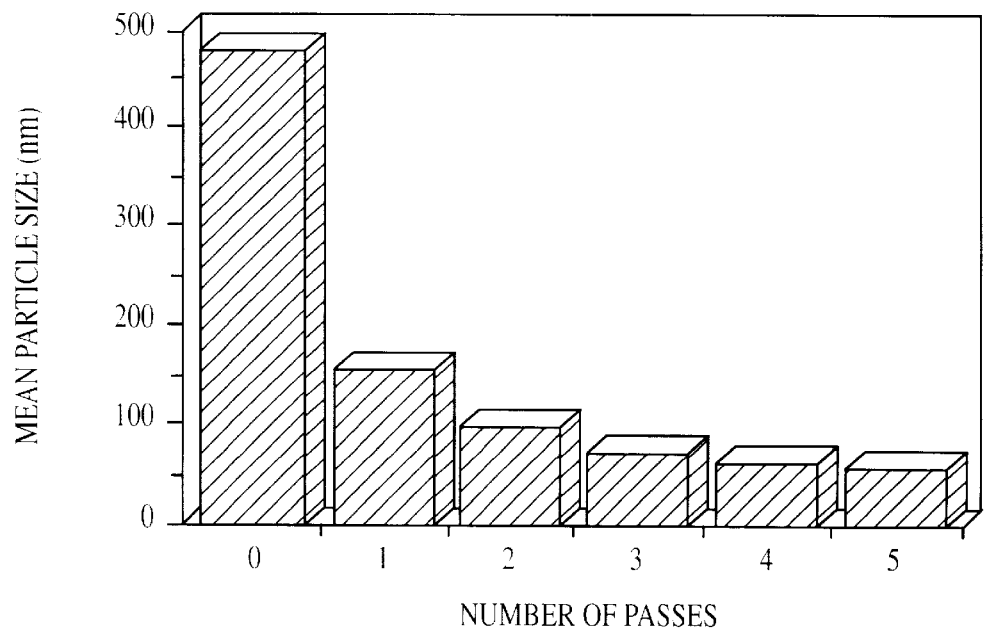
FIG. 10 shows the effect of homogenization passes on mean particle size of SLPs.

FIG. 10 presents the influence of the number of homogenization passes on the mean particle size of SLPs which is decreasing with increasing number of passes.

Example 10

Preparation of SLPs by probe sonication—Influence of sonication time on the mean particle size of SLPs In a sonication vial thermostatized at 80° C. 1.20 g tripalmitate is melted. In the lipid melt 0.40 g soy bean lecithin (Lipoid S 100) is dispersed by probe sonication until the dispersion appears optically clear. 0.60 g tyloxapol and 4 mg thiomersal is dissolved in bidistilled water heated to 80° C. The aqueous phase is added to the lipid melt and an SLP dispersion is prepared by probe sonication at 80° C. The sonicator operates at 50% of its maximum power. At certain time intervals (1, 5, 10 and 15 minutes) samples are taken from the dispersion for size measurements. After 30 minutes probe sonication is stopped and the dispersion is allowed to stand at room temperature to cool off.

Figure 11:
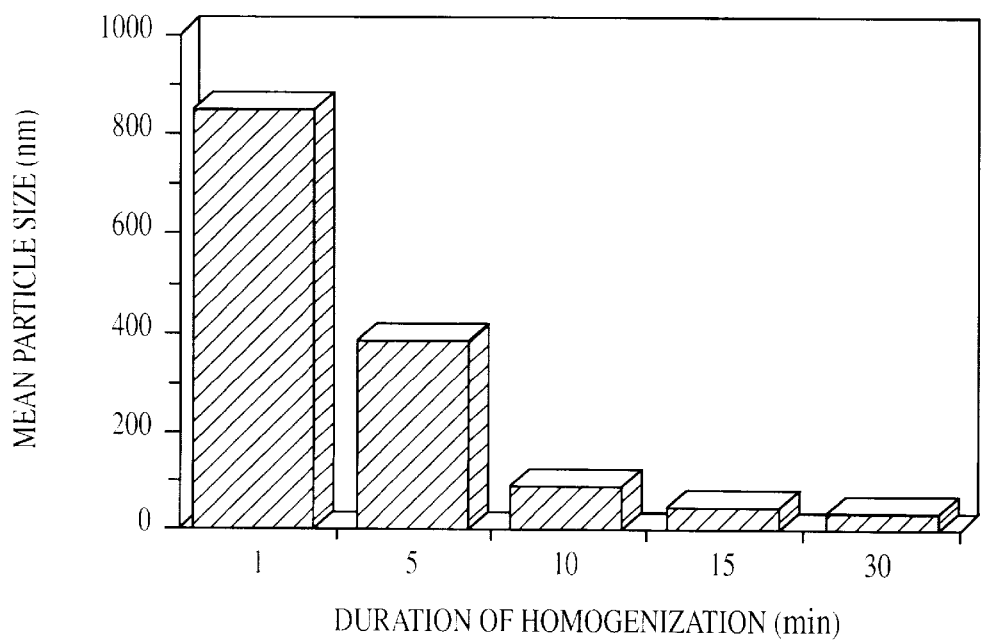
FIG. 11 shows the effect of sonication duration on mean particle size of SLPs.

The influence of sonication time on the mean particle size of the SLPs is displayed in FIG. 11. With increasing sonication time the mean particle size is decreasing and the size distribution becomes more narrow.

Example 11

Preparation of SLPs by stirring

An SLP dispersion composed as in Examples 9 and 10 is prepared by use of a heated magnetic stirrer (Pyro-Magnestir, Lab-Line). The lecithin is dispersed in the tripalmitate as described before. The heated aqueous phase is added to the melt. A dispersion is produced by stirring the mixture for 30 minutes at a temperature of 80° C. The dispersion is allowed to stand at room temperature to cool off.

The mean particle size after preparation (by volume) of the SLP dispersion is 59.5 µm determined by laser diffractometry (Malvern Mastersizer MS20). The maximum particle size measured is 250 µm. In contrast to high pressure homogenization and probe sonication, stirring produces relatively large particles in the micrometer size range.

Example 12

Influence of the matrix constituent on the mean particle size of SLPs

SLP dispersions composed of 10% matrix constituent, 1.2% soy bean lecithin (Lipoid S 100), 0.4% sodium glycocholate, 2.25% glycerol and 0.01% thiomersal in bidistilled water to 100% are prepared as described in Example 1. Five different matrix constituents are employed: the waxes cetylpalmitate and white bees-wax and the triglycerides trilaurate, trimyristate and tripalmitate.

Table 2 presents the PCS mean particle sizes of the different SLP dispersions and the melting points of the matrix constituents.

TABLE 2

Influence of matrix constituents.

| Matrix | Melting point (° C.) | Mean size of SLPs (nm) |
|---|---|---|
| Cetylpalmitate | 45.5 | 141.0 |
| White bees-wax | 62.5 | 195.3 |
| Trilaurate | 45.0 | 137.2 |
| Trimyristate | 56.5 | 161.1 |
| Tripalmitate | 63.0 | 209.2 |

The mean particle size of SLPs is increasing with the melting point of the matrix constituent.

Example 13

Influence of emulsifier type and amount on the mean particle size and stability of SLPs Tripalmitate SLP dispersions with different types and amounts of emulsifiers are prepared as described in Example 2. The composition of the different batches is given in Table 3. All dispersions contain 2.25% glycerol and 0.01% thiomersal.

Figure 12:
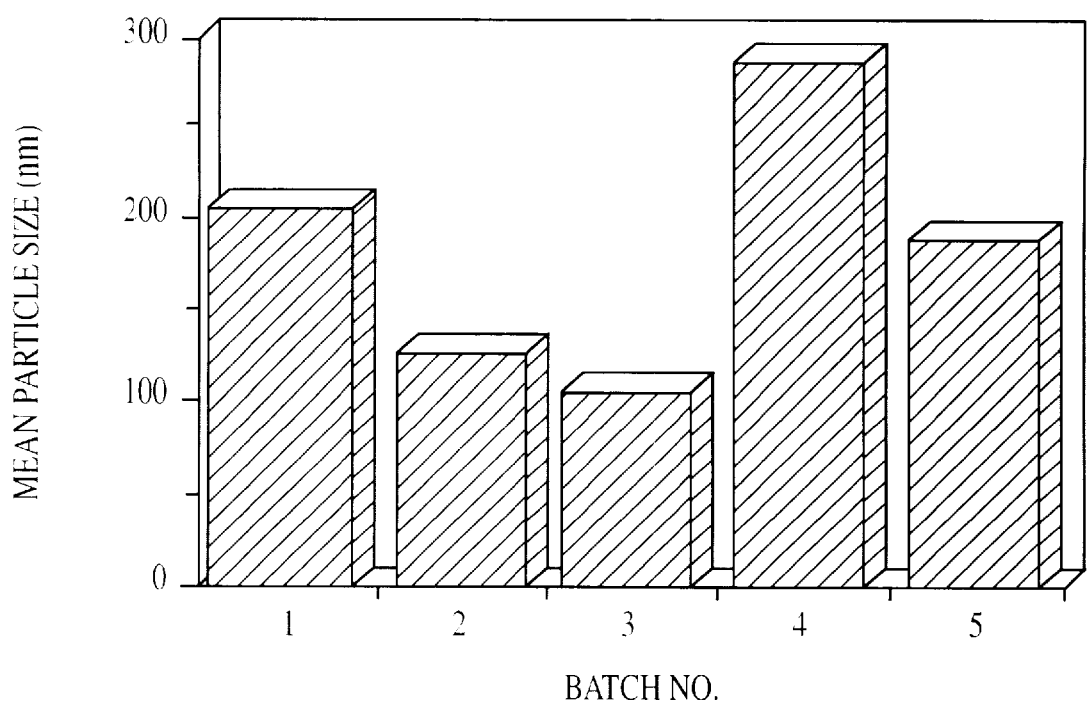
FIG. 12 shows the effect of type and amount of emulsifier on mean particle size of SLPs.

The mean particle size of the different batches of SLPs is presented in FIG. 12. The mean particle size depends on the type and amount of emulsifier.

TABLE 3

Compositions of SLP batches (in w %).

| Batch no | TP | PL | SGC | Plu |
|---|---|---|---|---|
| 1 | 10% | 1.2% | — | — |
| 2 | 10% | 1.2% | 0.4% | — |
| 3 | 10% | 2.4% | 0.4% | — |
| 4 | 10% | — | — | 1.8% |
| 5 | 10% | — | — | 3.6% |

Abbreviations; TP = tripalmitate, PL = phospholipids (Lipoid S 100), SGC = sodium glycocholate, Plu = Pluronic F68.

The combination of phospholipids and bile salts is most efficient with regard to the mean particle size and the stability. The system stabilized by phospholipids only gelatinizes and forms an ointment-like semi-solid gel on storage. The systems stabilized by Pluronic F68 tend to gelatinize when shear forces are applied, i e when the particles are forced to get closer to each other. Obviously the steric stabilization by poloxamers is not sufficient in this case. As a result the optimum stabilization is that by a surfactant combination of emulsifiers that are present in and act from the lipid side (such as phospholipids) and of emulsifiers that constitute a reservoir of highly mobile surfactant molecules in the dispersion medium (such as bile salts, tyloxapol and poloxamers). Though repulsion forces represent an important factor for the long-term stability, the basic mechanism of SLP stabilization is the high mobility of the excess of surfactant which provides for the immediate surface coverage of newly created surfaces during recrystallization of the molten lipids.

Example 14

Effect of bile salt as co-emulsifier of phospholipid stabilized SLPs

Phospholipid-stabilized SLP dispersions employing different matrices (tripalmitate, hard fat) are prepared with or without the addition of bile salt (sodium glycocholate) to the aqueous phase according to the method described in Example 1. All dispersions contain 2.25% glycerol and 0.01% thiomersal. Emulsification of the crude dispersions is performed by high pressure homogenization (APV Gaulin Micron Lab 40) under different homogenization conditions. The following dispersions were prepared:

| Composition | Homogenization conditions |
| --- | --- |
| 7.0 g TP, 0.84 g PL, 62.2 g $H_2O$ | 3 × 500 bar |
| 7.0 g TP, 0.84 g PL, 0.28 g BS, 61.9 g $H_2O$ | 3 × 500 bar |
| 7.0 g TP, 0.84 g PL, 62.2 g $H_2O$ | 10 × 1200 bar |
| 7.0 g TP, 0.84 g PL, 0.28 g BS, 61.9 g $H_2O$ | 10 × 1200 bar |
| 7.0 g HF, 0.84 g PL, 62.2 g $H_2O$ | 3 × 500 bar |
| 7.0 g HF, 0.84 g PL, 0.28 g BS, 61.9 g $H_2O$ | 3 × 500 bar |
| 7.0 g HF, 0.84 g PL, 62.2 g $H_2O$ | 10 × 1200 bar |
| 7.0 g HF, 0.84 g PL, 0.28 g BS, 61.9 g $H_2O$ | 10 × 1200 bar |

Abbreviations: BS = bile salt; $H_2O$ = bidistilled water, HF = hard fat (Witepsol W35); PL = phospholipids (Lipoid S 100); TP = tripalmitate.

Figure 13:
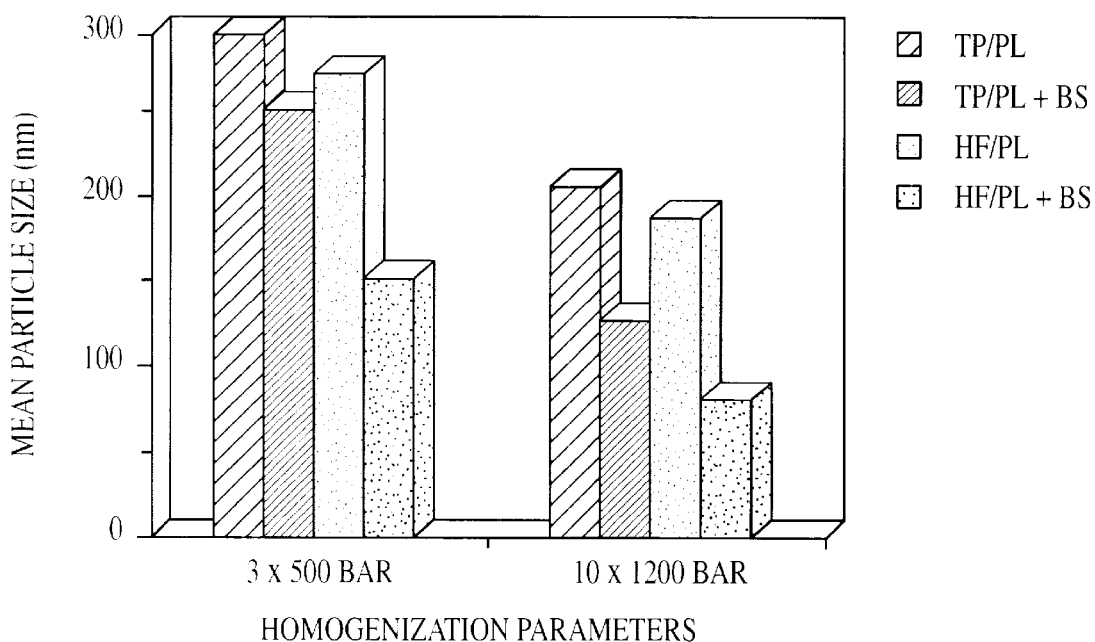
FIG. 13 shows the effect of homogenization parameters on mean particle size of various SLPs.

The mean particle size of the dispersions as determined by PCS after preparation is presented in FIG. 13. This example demonstrates the effect of bile salts as co-emulsifier in the aqueous phase on the particle size of phospholipid stabilized SLPs. It is clearly shown that the addition of bile salts reduces the mean particle size of SLPs by up to 57%. Thus, by the use of bile salts as co-emulsifier extremely fine dispersions can be obtained. The effect of the bile salt can be attributed to the high mobility of this micelle forming ionic surfactant which enables the surfactant molecules to immediately cover freshly generated surfaces during the homogenization process. The phospholipids which tend to form liquid crystalline structures in the aqueous phase are not sufficiently mobile to provide the immediate stabilization of freshly created particles so that instantaneous coalescence occurs in case there is no highly mobile co-surfactant in the aqueous phase.

Example 15

Preparation of trimyristate SLPs stabilized by a lecithin/bile salt blend

In a thermostatized vial 7.0 g trimyristate (Dynasan 114, Hüls AG) is melted at 70° C. 0.96 g phospholipids (Lipoid S 100) are dispersed in the melt by probe sonication. A solution of 280 mg sodium glycocholate, 1.6 g glycerol and 7 mg thiomersal in 61 ml bidistilled water is heated to 70° C. and added to the melt. A crude dispersion is prepared by probe sonication for approximately 2 minutes. The crude dispersion is transferred to a high pressure homogenizer (APV Gaulin Micron Lab 40) thermostatized at approximately 90° C. and is passed 5 times through the homogenizer at a pressure of 500 bar. The homogenized dispersion is allowed to stand at room temperature to cool off.

The mean particle size after preparation determined by PCS is 155.7 nm. In laser diffractometry (Malvern Mastersizer MS20) no particles above 1 μm can be detected. The particle size distribution derived from laser diffractometry is presented in FIG. 14. This example demonstrates that the use of bile salts as co-emulsifier of phospholipid stabilized SLPs efficiently prevents the formation of particles larger than 1 μm due to the rapid coverage of freshly created surfaces during homogenization, thereby minimizing immediate coalescence.

Example 16

Preparation of tripalmitate SLPs without ultrasonication (method A)

In a thermostatized vial 4.0 g tripalmitate (Dynasan 116, Hüls AG) is melted at 85° C. 0.96 g lecithin (Lipoid S 100) is dissolved in ethanol. The lecithin solution is added to the melt. The ethanol is evaporated at a temperature of 85° C. 160 mg sodium glycocholate, 0.9 g glycerol and 4 mg thiomersal is dissolved in 35 ml bidistiled water. The solution is heated to 85° C. and added to the melt. A crude dispersion is prepared by ultra-turrax vortexing for approximately 2 minutes. The crude dispersion is transferred to a high-pressure homogenizer (APV Gaulin Micron Lab 40) thermostatized at approximately 90° C. and passed 10 times through the homogenizer at a pressure of 800 bar. The homogenized dispersion is allowed to stand at room temperature to cool off.

Example 17

Preparation of tripalmitate SLPs without ultrasonication (method B)

In a thermostatized vial 4.0 g tripalmitate (Dynasan 116, Hüls AG) is melted at 85° C. 0.96 g lecithin (Lipoid S 100) is added to the melt. The mixture is shaken until the lecithin is completely dispersed in the melt and the dispersion appears isotropic. 160 mg sodium glycocholate, 0.9 g glycerol and 4 mg thiomersal is dissolved in 35 ml bidistilled water. The solution is heated to 85° C. and is added to the melt. A crude dispersion is prepared by ultra-turrax vortexing for approximately 2 minutes. The crude dispersion is transferred to a high-pressure homogenizer (APV Gaulin Micron Lab 40) thermostatized at approximately 90° C. and passed 10 times through the homogenizer at a pressure of 800 bar. The homogenized dispersion is allowed to stand at room temperature to cool off.

Example 18

Preparation of tripalmitate SLPs by dispersing phospholipids in the aqueous phase In a thermostatized vial 4.0 g tripalmitate (Dynasan 116) is melted at 80° C. 0.96 g phospholipids (Lipoid S 100) is dispersed in 35 ml of an aqueous solution of 160 mg sodium glycocholate, 0.9 g glycerol and 4 mg thiomersal by stirring for approximately one hour. The phospholipid dispersion is heated to 80° C. and added to the tripalmitate melt. A crude dispersion is prepared by probe sonication for approximately 2 minutes. The crude dispersion is transferred to a high-pressure homogenizer (APV Gaulin Micron Lab 40) thermostatized at approximately 90° C. and passed 10 times through the homogenizer at a pressure of 800 bar. The homogenized dispersion is allowed to stand at room temperature to cool off.

Example 19

Preparation of tripalmitate SLPs stabilized by a highly mobile surfactant

In a thermostatized vial 5.0 g tripalmitate is melted at 80° C. 600 mg sodium glycocholate is dissolved in 44.4 g bidistilled water containing 1.13 g glycerol and 0.01% thiomersal. The aqueous solution is heated to 80° C. and added to the melt. A crude dispersion is prepared by sonication for approximately 5 minutes. The crude dispersion is transferred to a thermostatized high-pressure homogenizer (APV Gaulin Micron Lab 40) and passed 8 times through the homogenizer at a pressure of 800 bar. The dispersion is allowed to stand at room temperature to cool off.

The mean particle size (by number) of the SLP dispersion after preparation is 96.8 nm determined by PCS. The size distribution is narrow and monomodal.

This example demonstrates that it is possible to prepare small homogenously sized SLPs by the use of one surfactant only, such as the bile salt sodium glycocholate, provided the surfactant is highly mobile and constitutes a reservoir of stabilizer in the aqueous phase in order to provide for the stabilization of newly created surfaces during recrystallization of the SLP matrix.

Example 20

Long-term stability of different SLP dispersions

Several different SLP dispersions are prepared according to the method described in Example 2. All dispersions contain 2.25% glycerol as isotonicity agent and 0.01% thiomersal as a preservative. The long-term stability of the dispersions is judged from repeated size measurements (by PCS) over a period of 18 months. The dispersions are stored at refrigeration temperatures. For comparison a soy bean oil emulsion system is included. The composition of the dispersions and their mean particle sizes during storage are summarized in Table 4.

TABLE 4

| Composition (w %) | | | Mean particle size (nm) after | |
|---|---|---|---|---|
| Matrix | PL | SGC | Preparation | 18 months |
| 10% TP | 1.2% | 0.4% | 125.9 | 121.6 |
| 10% TP | 2.4% | 0.4% | 104.5 | 111.2 |
| 10% TP | 2.4% | 0.4% | 103.6 | 104.7 |
| 9.5% TP[1]  0.5% GMS | 2.4% | 0.4% | 102.4 | 102.4 |
| 10% SO | 2.4% | 0.4% | 129.6 | 139.9 |

Abbreviations: PL = phospholipid (Lipoid S 100); SGC sodium glycocholate; TP = tripalmitate; GMS = glycerol monostearate; SO = soy bean oil.
[1]The SLP dispersion contains 5% (related to fat phase) of the cardioprotective drug ubidecarenone.

It is shown that the mean particle size of the dispersions remains practically unchanged during storage for 18 months. Thus, the results demonstrate that drug-free and drug-loaded SLP dispersions exhibit a long-term stability similar to that of lipid emulsions.

Example 21

Sterile filtration of tripalmitate SLPs 40 ml of a crude SLP dispersion composed of 3% tripalmitate (Dynasan 116, Hüls AG), 1.5% tyloxapol, 1% lecithin (Lipoid S 100), 2.25% glycerol and 0.01% thiomersal in bidistilled water to 100% is prepared according to the method described in Example 6. The crude dispersion is passed 5 times through a thermostatized homogenizer (APV Micron Lab 40) at a pressure of 1200 bar. Half the volume of the batch is allowed to stand at room temperature to cool off, whereas the rest is filtered through a sterile syringe filter (Nalgene SFCA, 0.2 μm pore size) before being cooled to the recrystallization temperature of the molten lipids.

The particle size distributon of both samples is determined by PCS. The mean particle size of the unfiltered sample is 56.7 nm and that of the sterile filtered SLP dispersion is 53.2 nm, i e both samples have practically the same mean particle size.

Example 22

Sterilization of tripalmitate SLPs by autoclaving 40 ml of a crude SLP dispersion composed of 3% tripalmitate (Dynasan 116, Hüls AG), 1.8% lecithin (Lipoid S 100), 0.6% sodium glycocholate, 2.25% glycerol and 0.01% thiomersal in bidistilled water to 100% is prepared according to the method described in Example 2. The crude dispersion is passed 10 times through a thermostatized homogenizer (APV Micron Lab 40) at a pressure of 1200 bar.

Before being cooled to the recrystallization temperature of the molten lipids the SLP dispersion is filled into an injection vial and sterilized by autoclaving at 121° C./2 atm for 45 minutes. The autoclaved dispersion is allowed to stand at room temperature to cool off. It shows no signs of aggregation or phase separation and has a mean particle size of 65.9 nm determined by PCS.

Example 23

Lyophilization of SLPs

In a thermostatized vial 3.5 g tripalmitate (Dynasan 116, Hüls AG) is melted at 75° C., and 1.05 g lecithin (Lipoid S 100, Lipoid KG) is dispersed in the melt by probe sonication. 1.58 g tyloxapol, 14 g sucrose and 7 mg thiomersal is dissolved in 50 ml bistilled water heated to 75° C. and the aqueous phase is added to the lipid melt. A crude dispersion is prepared by probe sonication and then passed 5 times through a thermostated high-pressure homogenizer (APV Gaulin Micron Lab 40) at a pressure of 900 bar. The homogenized dispersion is passed through a 0.2 μm sterile filter.

For lyophilization the dispersion is filled into planebottom vials which are immersed in liquid nitrogen for 1 minute and transferred to the freeze-drying chamber. Samples are freeze-dried for 36 hours under vacuum at a recipient temperature of −40° C.

Freeze-drying yields easily redispersible fine powders. The particle size of the SLP dispersions is determined by PCS prior to lyophilization and after reconstitution of the lyophilized powders with bistilled water. The mean particle size prior to lyophilization is 79 nm and that of the reconstituted dispersion is 87 nm, i e there is practically no change in mean particle size after lyophilization.

Example 24

Surface modification by adsorption of polymers

In a thermostalized vial 4.0 g tripalmitate (Dynasan 116, Hüls AG) is melted at 80° C. and 1.6 g soy bean lecithin (Lipoid S 100) is dispersed in the melt by probe sonication. 35.25 g of an aqueous solution of 0.01% thiomersal is heated to 80° C. and added to the melt. A crude dispersion is produced by probe sonication which is then passed five times through a high-pressure homogenizer at a pressure of 1200 bar. The dispersion is filtered through a 0.2 μm syringe filter. The batch is divided into 3 parts of equal volumes. One part is diluted with the same amount of water and stored at 90° C. to prevent gelation of the phospholipid stabilized dispersion on cooling down below the recrystallization temperature. The other two parts of the batch are incubated overnight with equal volumes of 6% (w/w) poloxamer 407 (Pluronic F127, BASF) and 6% (w/w) poloxamine 908 (Tetronic 908, BASF) solution, respectively, in such a way that the polymer solution is added to the SLP dispersion prior to being cooled below the recrystallization temperature of SLPs to provide for the immediate availability of polymer molecules as soon as new surfaces are created due to recrystallization. Both polymers have been described in literature to modify the biodistribution of intravenously administered colloidal particles.

The modification of the surface properties of tripalmitate SLPs is demonstrated by differences in the zetapotential. Zetapotentials were determined by laser Doppler anemometry in a microelectrophoresis cell (Malvern Zetasizer 3). The results are summarized in Table 5.

TABLE 5

Zetapotential of surface modified SLPs.

| Composition [% (w/w)] | | | Zetapotential |
|---|---|---|---|
| TP | PL | Polymer | [mV] |
| 5% | 2% | — | −29.6 |
| 5% | 2% | 3% F127 | −1.9 |
| 5% | 2% | 3% T908 | −2.9 |

Abbreviations: TP = tripalmitate, PL = phospholipids, F127 = PLURONIC F127, T908 = Tetronic 908.

The incubation of SLPs with block copolymers of the poloxamer and poloxamine type results in a decrease of the zetapotential. Due to the adsorption of the polymers the surfaces become more hydrophobic. The hydrophobicity of the surface is described to be one of the factors governing the RES (reticuloendothelial system) activity and the biodistribution of colloidal particles.

Example 25

Preparation of SLPs loaded with the cardio-protective drug ubidecarenone

Three different types of SLPs containing the cardio-protective drug ubidecarenone are prepared. The SLPs are composed as summarized in table 6. All dispersions contain 2.25% glycerol and 0.01% thiomersal.

Batch 1 and 2 are prepared by dispersing lecithin in the molten matrix constituent as described before. In this melt ubidecarenone is dissolved. After addition of the aqueous phase containing sodium glycocholate, glycerol and thiomersal a crude dispersion is prepared by probe sonication. It is transferred to a thermostatized homogenizer (APV Micron Lab 40) and passed through the homogenizer ten times at a pressure of 800 bar. The dispersions are allowed to stand at room temperature to cool off.

Batch 3 is prepared by dispersing lecithin in the molten matrix constituent as described before. In this melt ubidecarenone is dissolved. After addition of the aqueous phase containing tyloxapol, glycerol and thiomersal, a crude dispersion is prepared by probe sonication. It is transferred to a thermostatized homogenizer (APV Micron Lab 40) and passed 5 times through the homogenizer at a pressure of 1200 bar. The dispersion is allowed to stand at room temperature to cool off.

TABLE 6

Ubidecarenone-loaded SLPs.

| Batch no | Composition | Mean particle size |
|---|---|---|
| 1 | 10% TP, 2.4% PL, 0.4% SGC, 1% Ubi | 80.2 nm |
| 2 | 10% HF, 1.2% PL, 0.4% SGC, 1% Ubi | 78.9 nm |
| 3 | 3% TP, 1.5% Tyl, 1% PL, 0.2% Ubi | 46.8 nm |

Abbreviations: TP = tripalmitate, PL = phospholipids, SGC = sodium glycocholate, Ubi = Ubidecarenone, HF = hard fat (Witepsol W35), Tyl = Tyloxapol.

Example 26

Preparation of SLPs loaded with oxazepam

In a thermostatized vial 7.0 g tripalmitate is melted at 80° C. 1.68 g lecithin and 140 mg oxazepam is dispersed in the melt by probe sonication. 60 ml of heated aqueous phase containing 280 mg sodium glycocholate, 1.58 g glycerol and 7 mg thiomersal is added to the melt and a crude dispersion is prepared by probe sonication. The crude dispersion is homogenized by passing 10 times through a thermostatized high-pressure homogenizer at a pressure of 800 bar. The dispersion is allowed to stand at room temperature to cool off. The dispersion of oxazepam loaded SLPs has a mean particle size of 122.7 nm after preparation.

Example 27

Preparation and long-term stability of SLPs loaded with diazepam

In a thermostatized vial 4.0 g tripalmitate is melted at 80° C. 0.96 g lecithin and 120 mg diazepam is dispersed in the melt by probe sonication. 35 ml of heated aqueous phase containing 160 mg sodium glycocholate, 0.9 g glycerol and 4 mg thiomersal is added to the melt and a crude dispersion is prepared by probe sonication. The crude dispersion is homogenized by passing 10 times through a thermostatized high-pressure homogenizer at a pressure of 800 bar. The dispersion is allowed to stand at room temperature to cool off.

The dispersion of diazepam-loaded SLPs has a mean particle size after preparation of 104.6 nm. After 12 months of storage the mean particle size determined by PCS is 113.9 nm. Precipitation of drug substance during storage is not detected macroscopically. Investigations of the dispersion by polarized light microscopy over the monitored period of 12 months do not reveal the presence of drug crystals.

Example 28

Preparation of SLPs loaded with lidocaine

In a thermostatized vial 4.0 g tripalmitate is melted at 80° C. 0.96 g lecithin and 60 mg lidocaine is dispersed in the melt by probe sonication. 35 ml of heated aqueous phase containing 320 mg sodium glycocholate, 0.9 g glycerol and 4 mg thiomersal is added to the melt and a crude dispersion is prepared by probe sonication. The crude dispersion is homogenized by passing 10 times through a thermostatized high-pressure homogenizer at a pressure of 800 bar. The dispersion is allowed to stand at room temperature to cool off.

The dispersion of lidocaine loaded SLPs has a mean particle size after preparation of 90.4 nm.

Example 29

Preparation and long-term stability of SLPs loaded with prednisolone

In a thermostatized vial 4.0 g tripalmitate is melted at 80° C. 0.48 g lecithin and 80 mg prednisolone is dispersed in the melt by probe sonication. 36 ml of heated aqueous phase containing 160 mg sodium glycocholate, 0.9 g glycerol and 4 mg thiomersal is added to the melt and a crude dispersion is prepared by probe sonication. The crude dispersion is homogenized by passing 10 times through a thermostatized high-pressure homogenizer at a pressure of 800 bar. The dispersion is allowed to stand at room temperature to cool off.

The dispersion of prednisolone-loaded SLPs has a mean particle size after preparation of 118.3 nm. After 12 months of storage the mean particle size determined by PCS is 124.2 nm. Precipitation of drug substance during storage is not detected macroscopically. Investigations of the dispersion by polarized light microscopy over the monitored period of 12 months do not reveal the presence of drug crystals.

Example 30

Preparation of SLPs loaded with cortisone

Four different types of SLPs containing cortisone are prepared. The SLPs are composed as summarized in table 7. All dispersions contain 2.25% glycerol and 0.01 thiomersal.

Batch 1 and 2 are prepared by dispersing lecithin in the molten matrix constituent as described before. In this melt cortisone is dissolved. After addition of the aqueous phase containing sodium glycocholate, glycerol and thiomersal, a crude dispersion is prepared by probe sonication. It is transferred to a thermostatized homogenizer (APV Micron Lab 40) and passed 10 times through the homogenizer. The dispersions are allowed to stand at room temperature to cool off.

Batch 3 is prepared by dispersing lecithin in the molten matrix constituent as described before. In this melt cortisone is dissolved. After addition of the aqueous phase containing poloxamer (Pluronic F68), glycerol and thiomersal, a crude dispersion is prepared by probe sonication. It is transferred to a thermostatized homogenizer (APV Micron Lab 40) and passed 5 times through the homogenizer at a pressure of 1200 bar. The dispersion is allowed to stand at room temperature to cool off.

Batch 4 is prepared by dispersing lecithin in the molten matrix constituent as described before. In this melt cortisone is dissolved. After addition of the aqueous phase containing tyloxapol, glycerol and thiomersal a crude dispersion is prepared by probe sonication. It is transferred to a thermostatized homogenizer (APV Micron Lab 40) and passed through the homogenizer five times at a pressure of 1200 bar. The dispersion is allowed to stand at room temperature to cool off.

TABLE 7

Cortisone-loaded tripalmitate SLPs.

| Batch no | Composition | Mean particle size |
|---|---|---|
| 1 | 10% TP, 1.2% PL, 0.4% SGC, 0.2% Cort | 124.2 nm |
| 2 | 3% TP, 1.8% PL, 0.6% SGC, 0.3% Cort | 67.3 nm |
| 3 | 10% TP, 4.5% Plu, 3% PL, 0.1% Cort | 70.5 nm |
| 4 | 3% TP, 1.5% Tyl, 1% PL, 0.1% Cort | 48.5 nm |

Abbreviations: TP = tripalmitate, PL = phospholipids, SGC = sodium glycocholate, Cort = Cortisone, Plu = Pluronic F68, Tyl = Tyloxapol.

Example 31

Tripalmitate SLPs loaded with retinol (vitamin A)

In a thermostatized vial 1.0 g tripalmitate (Dynasan 116, Hüls AG) is melted at 80° C. 60 mg retinol (vitamin A-alcohol>99%, Fluka) is dissolved in the melt. 300 mg soy bean lecithin (Lipoid S 100) is dispersed in the melt by probe sonication until the dispersion appears optically clear. 450 mg poloxamer 407 (Pluronic™ F127, BASF) is dissolved in 29.0 g bidistilled water. The aqueous phase is heated to 80° C. and added to the melt. A fine dispersion is prepared by probe sonication for 20 minutes. The dispersion is filtered through a 0.2 μm syringe filter to remove metal shed from the ultrasound probe. The dispersion is allowed to stand at room temperature to cool off.

The mean particle size by number after preparation of vitamin A-loaded tripalmitate SLPs is 98.5 nm determined by PCS.

Example 32

Tripalmitate SLPs loaded with phytylmenadione (vitamin $K_3$)

In a thermostatized vial 1.0 g tripalmitate (Dynasan 116, Hüls AG) is melted at 80° C. 60 mg phytylmenadione (vitamin $K_3$, Sigma) and 300 mg soy bean lecithin (Lipoid S 100) is dispersed in the melt by probe sonication until the dispersion appears optically clear. 450 mg poloxamer 407 (Pluronic™ F127, BASF) is dissolved in 28.7 g bidistilled water. The aqueous phase is heated to 80° C. and added to the melt. A fine dispersion is prepared by probe sonication for 20 minutes. The dispersion is filtered through a 0.2 μm syringe filter to remove metal shed from the ultrasound probe. The dispersion is allowed to stand at room temperature to cool off. The mean particle size by number after preparation of vitamin $K_3$-loaded tripalmitate SLPs is 86.8 nm determined by PCS.

Example 33

Preparation of tripalmitate SLPs loaded with estramustine

In a termostatized vial 7.0 g tripalmitate (Dynasan 116, Hüls AG) is melted at 80° C. In the melt 1.68 g soy bean lecithin (Lipoid S 100) is dispersed by probe sonication until the dispersion appears optically clear. 40 mg estramustine is dissolved in the tripalmitate/lecithin dispersion. 0.42 g sodium glycocholate and 1.58 g glycerol is dissolved in 60 g bidistilled water. The aqueous phase is heated to 80° C. and added to the melt. A crude emulsion is prepared by probe sonication for approximately 2 minutes. The crude emulsion is transferred to a thermostatized high-pressure homogenizer (APV Gaulin Micron Lab 40) and passed 10 times through the homogenizer at a pressure of 800 bar. The dispersion is allowed to stand at room temperature to cool off.

Example 34

Physical state of different SLPs at body temperature

Two batches of SLPs from different matrix constituents are prepared according to the method described in Example 2. Batch 1 is composed of 10% tripalmitate, 0.5% ubidecarenone, 1.2% soy bean lecithin (Lipoid S 100, Lipoid KG), 0.4% sodium glycocholate, 2.25% glycerol, 0.01% thiomersal and bidistilled water to 100% (by weight). Batch 2 is composed of 10% hard fat (Witepsol™ W35, Hüls AG), 0.5% ubidecarenone, 1.2% soy bean lecithin (Lipoid S 100, Lipoid KG), 0.4% sodium glycocholate, 2.25% glycerol, 0.01% thiomersal and bidistilled water to 100% (by weight).

The physical state of the matrix constituents is determined by synchrotron radiation X-ray diffraction at 20° C. and at 38° C. The samples are placed in thermostatized sample holders. The diffraction patterns are recorded for 180 seconds each. FIG. 15a demonstrates that at room temperature (20° C.) both batches of SLPs are crystalline. The spacings correspond to the $\alpha$ crystalline polymorphs. At body temperature (38° C.) the tripalmitate SLPs are still crystalline whereas no reflections can be detected for the hard fat SLPs, i e they are amorphous and molten (FIG. 15b). The different physical states of these SLPs at body temperature give rise to a different biopharmaceutical behaviour with respect to the release of incorporated drugs or bioactive agents. SLPs molten at body temperature display basically the release characteristics typical of conventional lipid emulsions. Due to the free diffusion of drug molecules in the liquid lipid the drug can be released from the vehicle relatively fast. In contrast, SLPs which are solid at body temperature give rise to sustained release of incorporated drugs. Since the drug molecules are immobilized in the solid matrix drug release is not diffusion-controlled but depends on the degradation of the solid lipid matrix in the body and is therefore delayed.

Example 35

Preparation of PBAs from miconazole

In a thermostatized vial 0.4 g miconazole is melted at 90° C. 0.24 g lecithin (Lipoid S 100) is dispersed in the melt by probe sonication until the dispersion appears optically clear. 0.9 g glycerol, 80 mg sodium glycocholate and 4 mg thiomersal is dissolved in 38.5 ml bidistilled water and heated to 90° C. The aqueous phase is added to the miconazole/lecithin melt and a crude dispersion is produced by probe sonication for 5 minutes. The crude dispersion is transferred to a thermostatized high-pressure homogenizer (APV Gaulin Micron Lab 40) and passed 10 times through the homogenizer at a pressure of 800 bar. The PBA dispersion is allowed to stand at room temperature to cool off.

On cooling the molten miconazole recrystallizes and forms a suspension of miconazole microparticles. The mean particle size (by volume) of miconazole PBAs is 21.8 μm determined by laser diffractometry. The sediment of miconazole PBAs is easily redispersible by slight agitation.

Example 36

Preparation of PBAs from ibuprofen

In a thermostatized vial 1.2 g ibuprofen is melted at 85° C. 0.72 g lecithin (Lipoid S 100) is dispersed in the melt by probe sonication until the dispersion appears optically clear. 0.9 g glycerol, 240 mg sodium glycocholate and 4 mg thiomersal is dissolved in 37 ml bidistilled water and heated to 85° C. The aqueous phase is added to the ibuprofen/lecithin melt and a crude dispersion is produced by probe sonication for 5 minutes. The crude dispersion is transferred to a thermostatized high-pressure homogenizer (APV Gaulin Micron Lab 40) and passed 6 times through the homogenizer at a pressure of 800 bar. The PBA dispersion is allowed to stand at room temperature to cool off.

On cooling the molten ibuprofen recrystallizes and forms a suspension of ibuprofen microparticles. The mean particle size (by volume) of ibuprofen PBAs is 61.4 μm determined by laser diffractometry. The sediment of ibuprofen PBAs is easily redispersible by slight agitation.

Example 37

Dissolution speed of ibuprofen PBAs

Figure 16:
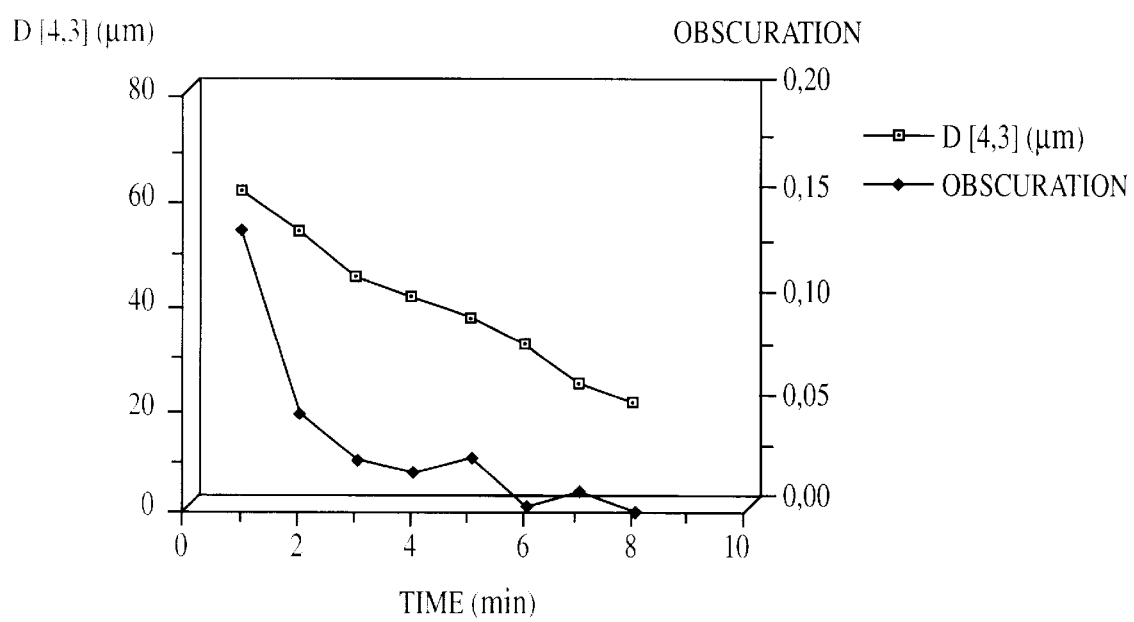
FIG. 16 shows the decay of obscuration and particle size of a sample of ibuprofen PBAs.

The dissolution speed of ibuprofen PBAs of Example 36 is measured in a laser diffractometer (Malvern Mastersizer MS20) by monitoring the decay of the so-called obscuration over a period of 10 minutes. The obscuration is a measure of the reduced intensity of unscattered laser light by a sample and is related to the concentration of particles in the laser beam. In parallel the particle size can be measured. For measurement the ibuprofen PBA sample is diluted with water and dispersed by magnetic stirring in a measuring cell placed in the laser beam line. FIG. 16 presents the decay of obscuration and particle size of a sample of ibuprofen PBAs. Within 10 minutes the obscuration has decayed to zero, i e there is no detectable amount of particles hinting at the complete dissolution of the PBAS. The dissolution of the untreated raw substance ibuprofen cannot be measured by this technique since the substance is only poorly wettable in water.

Example 38

Preparation of PBAs from lidocaine

In a thermostatized vial 1.2 g lidocaine is melted at 80° C. 1.2 g tyloxapol is dissolved in 37.6 ml bidistilled water and heated to 80° C. The aqueous phase is added to the lidocaine melt and a crude dispersion is produced by probe sonication for 2 minutes. The crude dispersion is transferred to a thermostatized high-pressure homogenizer (APV Gaulin Micron Lab 40) and passed 5 times through the homogenizer at a pressure of 1200 bar. The PBA dispersion is allowed to stand at room temperature to cool off.

Figure 17:
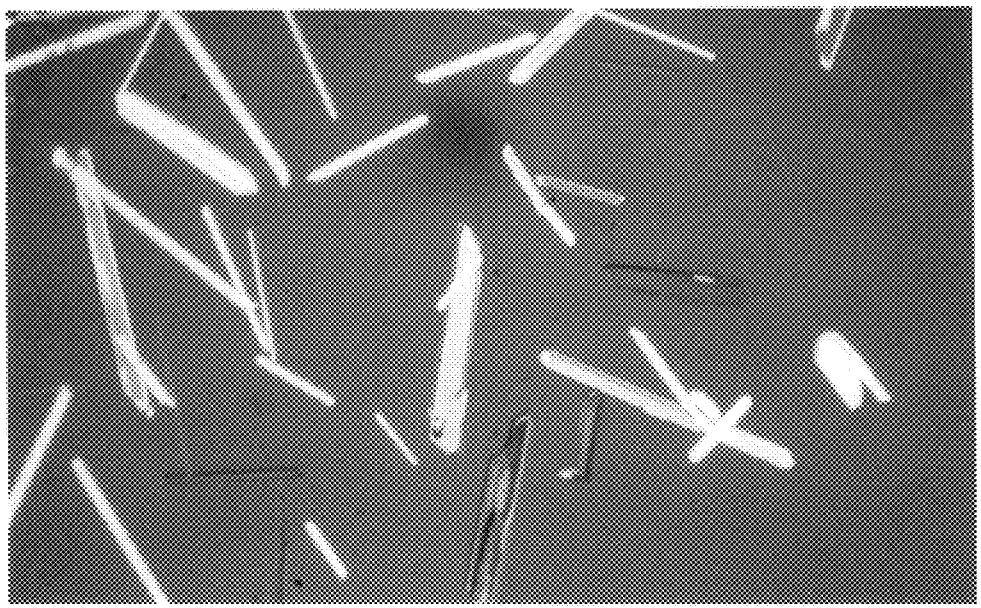
FIG. 17 is a polarized microscopic picture of lidocaine PBAs.

On cooling the molten lidocaine recrystallizes into fine needles and forms a suspension of lidocaine microparticles. FIG. 17 shows a polarized microscopic picture of the suspended lidocaine needles. The particle shape of the raw material lidocaine-base (Synopharm) is different from that of lidocaine PBAs as demonstrated by the polarized microscopic picture of FIG. 18.

The mean particle size (by volume) of lidocaine PBAs is 174.2 μm determined by laser diffractometry. The maximum detected particle size is 400 μm. The sediment of lidocaine PBAs is easily redispersible by slight agitation. The addition of water to PBAs leads to the rapid dissolution of the particles. In contrast the raw material lidocaine is only sparingly soluble in water and the dissolution speed is much slower. The high dissolution speed of lidocaine PBAs is a consequence of the modified surface properties and the finely dispersed state of the particles. Due to the rapid dissolution a determination of the dissolution speed according to the method described in Example 37 is not possible.

Example 39

Preparation of PBAs from cholecalciferol (vitamin D$_3$)

In a thermostatized vial 0.8 g cholecalciferol is melted at 95° C. 120 mg soy bean lecithin (Lipoid S 100) is dispersed in the melt by probe sonication until the dispersion appears optically clear. 40 mg sodium glycocholate and 0.9 g glycerol is dissolved in 37.92 ml bidistilled water and heated to 95° C. The aqueous phase is added to the cholecalciferol/lecithin dispersion and a crude dispersion is produced by probe sonication for 5 minutes. The crude dispersion is transferred to a thermostatized high-pressure homogenizer (APV Gaulin Micron Lab 40) and passed 8 times through the homogenizer at a pressure of 1200 bar. The PBA dispersion is allowed to stand at room temperature to cool off.

The mean particle size after preparation by number of cholecalciferol PBAs is 325.1 nm determined by PCS.

Example 40

Preparation of PBAs from estramustine

In a thermostatized vial 2 g estramustine is melted at 105° C. In the melt 0.8 g soy bean lecithin (Lipoid S 100) is dispersed by probe sonication until the dispersion appears optically clear. 0.2 g sodium glycocholate and 0.9 g glycerol is dissolved in 36.1 g bidistilled water. The aqueous phase is heated to 95° C. and added to the melt. A crude emulsion is prepared by probe sonication for approximately 5 minutes. The crude emulsion is transferred to a thermostatized high-pressure homogenizer (APV Gaulin Micron Lab 40) and passed 5 times through the homogenizer at a pressure of 1200 bar. The dispersion is allowed to stand at room temperature to cool off.

LEGENDS OF FIGURES

Figure 4:
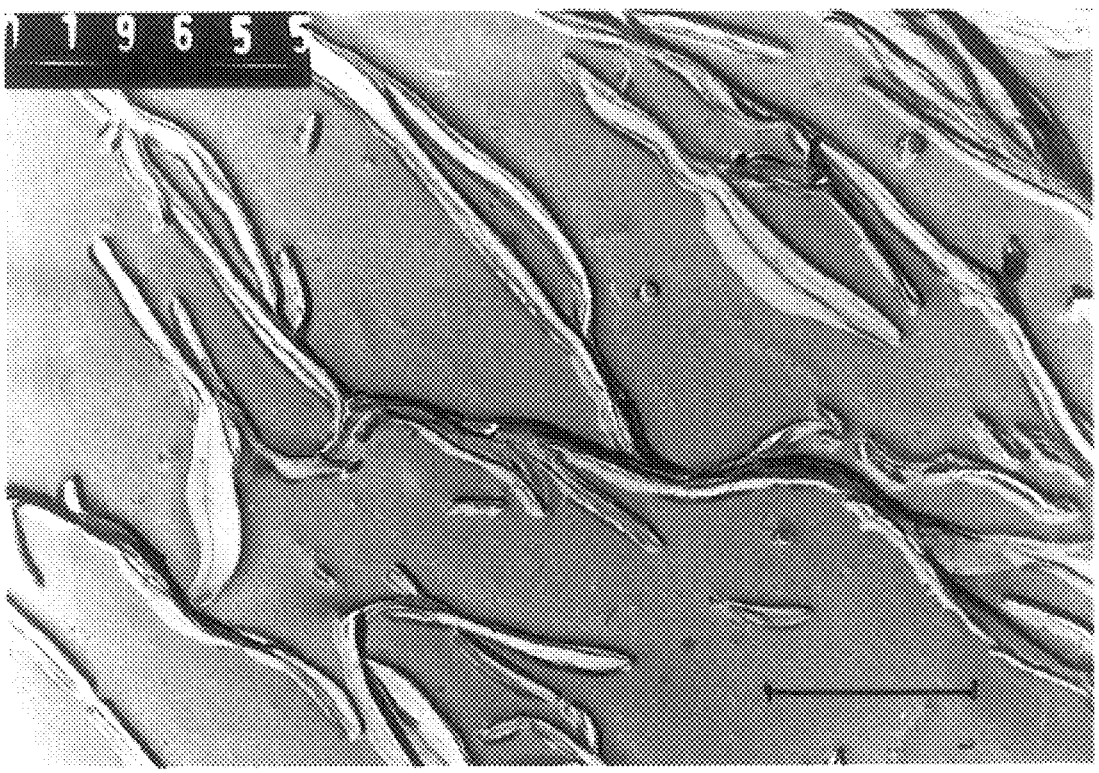
FIG. 4 is a transmission electron micrograph of a SLP preparation which has become a turbid semi-solid, ointment-like gel.
Figure 6:
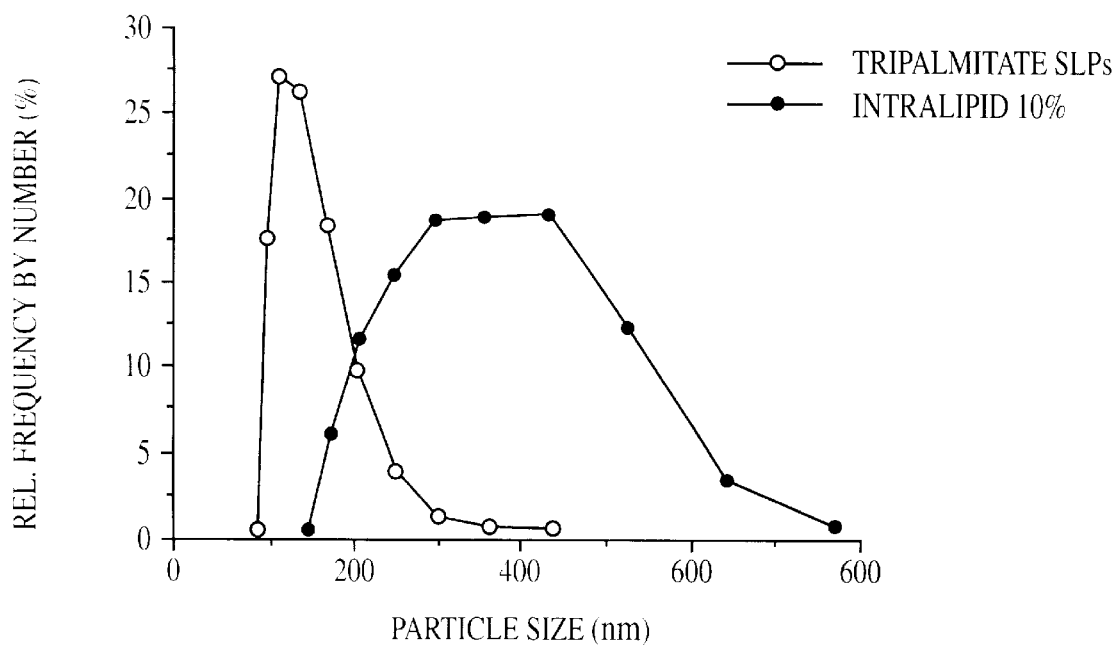
FIG. 6 is the PCS particle size distribution of tripalmitate SLPs and 10% INTRALIPID.
Figure 14:
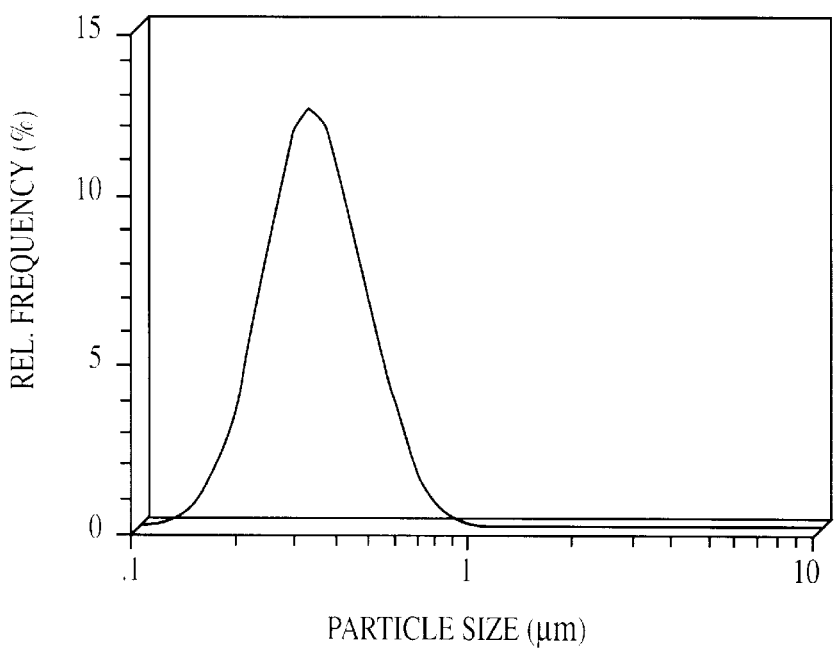
FIG. 14 shows the laser diffractometry determination of particle size distribution of SLPs.

Fig. 1 Transmission electron micrograph of tripalmitate SLPs of Example 1 after 5 months of storage at room temperature. The bar represents 400 nm.
Fig. 2 Differential scanning calorimetric (DSC) thermogram of a) pure tripalmitate and of b) tripalmitate SLPs of Example 1. The transition peaks correspond to the melting of the $\beta$ crystalline polymorph.
Fig. 3 Synchrotron radiation wide angle X-ray diffraction pattern of tripalmitate SLPs of Example 2. The reflexions correspond to the $\beta$ crystalline polymorph.
Fig. 4 Transmission electron micrograph of unstable hard fat SLPs of Example 5. The SLP dispersion gelatinized on storage by forming a three-dimensional network. The bar corresponds to 1000 nm.
Fig. 5 Particle size distribution of tripalmitate SLPs of Example 1 after 15 months of storage. The graph represents the result of a multiangle PCS measurement.
Fig. 6 PCS particle size distribution of a 10% tripalmitate SLP dispersion compared to that of the commercial lipid emulsion Intralipid ® 10%.
Fig. 7 Influence of microfluidization time on the mean particle size of hard fat SLPs of Example 3.
Fig. 8 Stability on storage of hard fat SLPs of Example 3 as indicated by the development of the mean particle size with storage time (monitored period: 12 months).
Fig. 9 Influence of homogenization pressure on the mean particle size of tripalmitate SLPs.
Fig. 10 Influence of the number of homogenization passes on the mean particle size of tripalmitate SLPs (no 0 corresponds to the crude dispersion prepared by sonication).
Fig. 11 Influence of sonication time on the mean particle size of tripalmitate SLPs prepared by probe sonication.
Fig. 12 Influence of type and amount of emulsifier on the mean particle size of tripalmitate SLPs prepared according to Example 13.
Fig. 13 Effect of bile salts as co-emulsifier on the mean particle size of different phospholipid stabilized SLP dispersions of Example 14.
Fig. 14 Particle size distribution of trimyristate SLPs of Example 15 as determined by laser diffractometry.

-continued

LEGENDS OF FIGURES

Figure 15:
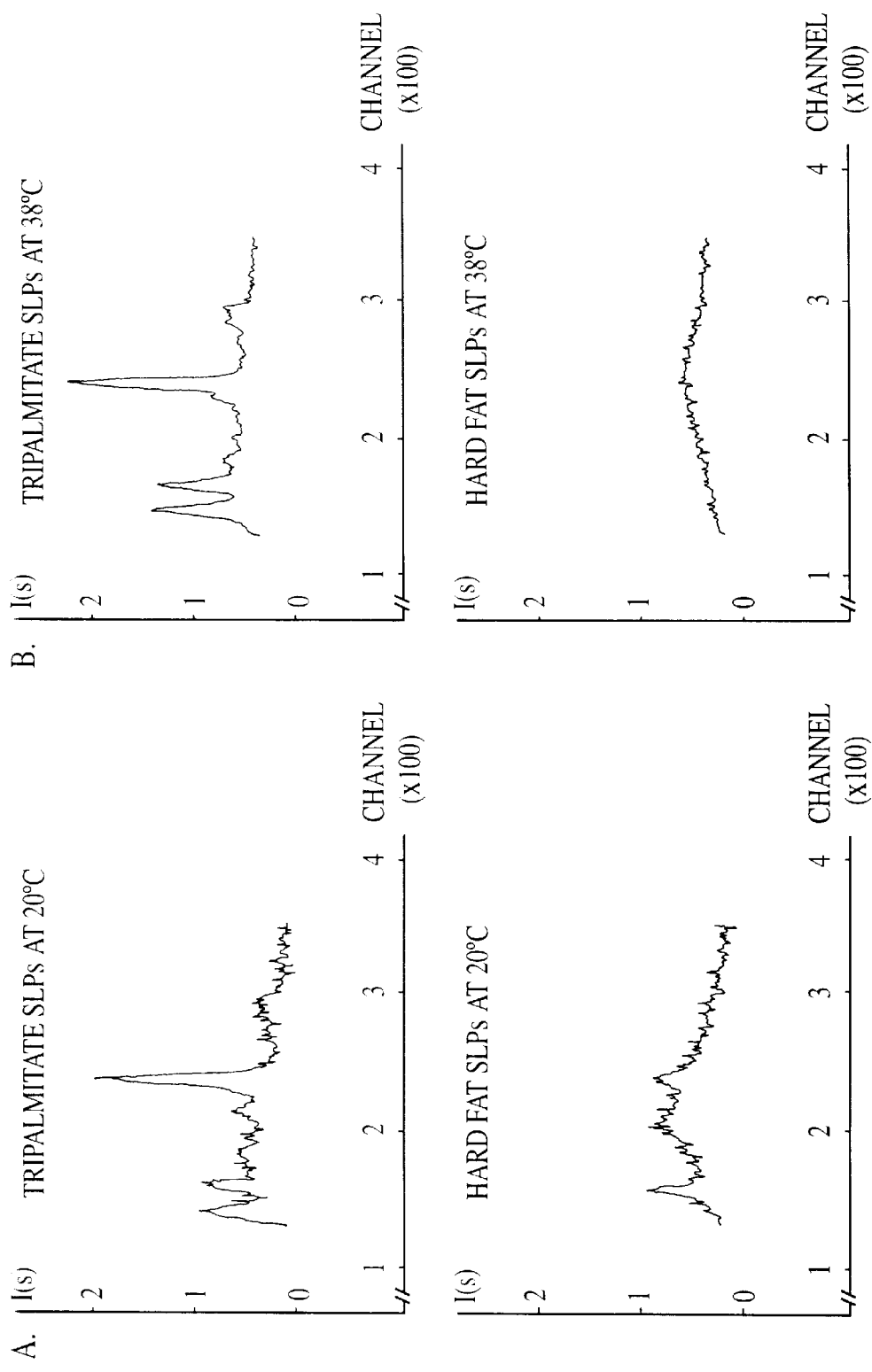
FIG. 15A shows the wide angle X-ray diffraction of tripalmitate SLPs and hard fat SLPs at 20° C.
FIG. 15B shows the wide angle X-ray diffraction of tripalmitate SLPs and hard fat SLPs at 38° C.
Figure 18:
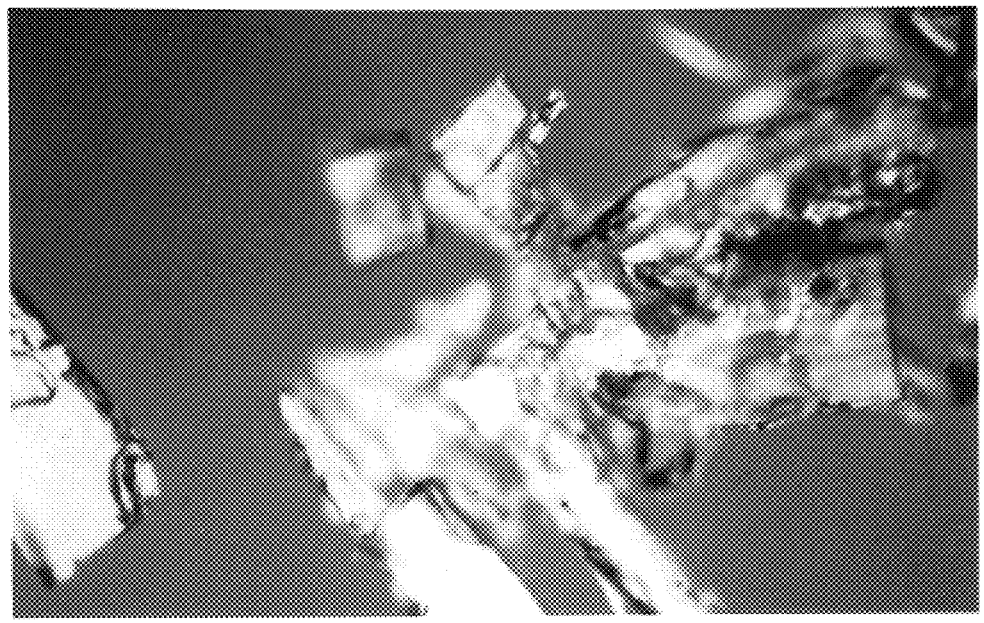
FIG. 18 is a polarized microscopic picture of lidocaine raw material.

Fig. 15 The physical state of different drug-loaded SLPs a) at 20° C. and b) at 38° C. determined by synchrotron radiation wide-angle X-ray diffraction.
Fig. 16 Dissolution speed of ibuprofen PBAs of Example 37.
Fig. 17 Polarized microscopic picture of Iidocaine PBAs of Example 38 (magnification: 150 x).
Fig. 18 Polarized microscopic picture of Iidocaine raw material employed for the production of Iidocaine PBAs (magnification: 150 x).

What is claimed is:

1. A suspension stable for at least about 12 months of particles of bioactive agents (PBAs) manufactured by an emulsifying process having the following steps:
    (a) melting at least one solid bioactive agent;
    (b) heating a dispersion medium to approximately the same temperature as said at least one molten solid bioactive agent formed by step (a);
    (c) adding at least one highly mobile water-soluble or dispersible stabilizer, which does not form a separate phase in the dispersion medium, to the dispersion medium in an amount effective after emulsification to stabilize newly created surfaces during recrystallization, and optionally adding at least one lipid-soluble or dispersible stabilizer to said at least one molten bioactive agent;
    (d) premixing said at least one molten bioactive agent and the dispersion medium, and subsequently homogenizing said mixture by high pressure homogenization, micro-fluidization and/or ultrasonication; and
    (e) allowing the homogenized dispersion to cool until solid particles are formed by recrystallization of the dispersed bioactive agents,
wherein the PBAs consist of a single phase, and include a drug having a low bioavailability and/or being poorly absorbed from the intestinum, and having a melting point below about 100° C. or which can be decreased to below about 100° C. or which can be decreased to below about 100° C. by addition of an adjuvant, which drug is selected from the group consisting of an anesthetic, a narcotic, an anticholinergic, an antidepressive, a physychostimulant, a neuroleptic, an antiepileptic, an antiphlogistic, a bronchodilator, a cardiovascular drug, a cytostatic, a hyperemic drug, a lipid reducer, a spasmolytic, a testosterone derivative, a tranquilizer, a virustatic, a vitamin A derivative, a vitamin E derivative, menadione, cholecalciferol, an insecticide, a pesticide, and a herbicide.

2. A suspension of particles of bioactive agents (PBAs) according to claim 1, wherein the PBAs are water-insoluble at the temperature of emulsion preparation and are not solubilized by an excess of stabilizers or form micelles by themselves, the particle size of the PBAs remaining unchanged before and after cooling to room temperature.

3. A suspension of particles of bioactive agents (PBAs) according to claim 1, wherein the PBAs are partly water-soluble at the temperature of emulsion preparation and/or are able to form mixed micelles with an excess of stabilizers and/or form micelles by themselves, leading to an increase of particle size after cooling to room temperature due to crystal growth and/or precipitation of dissolved bioactive agent and/or due to mass transport from smaller to larger particles.

4. A suspension of particles of bioactive agents (PBAs) manufactured according to claim 1, wherein said drug is selected from the group consisting of butanilicaine, fomocaine, isobutambene, lidocaine, risocaine, prilocaine, pseudococaine, tetracaine, trimecaine, tropacocaine, etomidate, metixen and profenamine, alimenazine, binedaline, perazine, chlorpromazine, fenpentadiol, fenanisol, fluanisol, mebenazine, methylphenidate, thioridazine, toloxaton, trimipramine, dimethadion, nicethamide, butoconazole, chlorphenesin, etisazole, exalamid, pecilocine, miconazole, butibufen, ibuprofen, bamifylline, alprenolol, butobendine, cloridazole, hexobendine, nicofibrate, penbutolol, pirmenol, prenylamine, procaine amide, propatylnitrate, suloctidil, toliprolol, xibendol, viquidile, asperline, chlorambucil, chlornaphhazine, mitotane, estramustine, taxol, penclomedine, trofosfamide, capsaicine, methylnicotinate, nicoclonate, oxprenolol, pirifibrate, simfibrate, thiadenol, aminopromazine, caronerine, difemerine, fencarbamide, tiropramide and moxaverine, testosterone enanthate, testosterone-(4-methylpentanoate), azaperone, buramate, arildon, retinol, retinol acetate, retinol palmitate, tocopherol acetate, tocopherol succinate, tocopherol nicotinate, menadione, cholecalciferol, acephate, cyfluthrin, azinphosphomethyl, cypermethrine, substituted phenyl thiophosphates, fenclophos, permethrine, piperonal, tetramethrine and trifluraline.

5. Liquid-free particles obtained by removing the dispersion medium from the suspension of claim 1 by filtration, ultrafiltration or freeze-drying.

* * * * *